(12) United States Patent
Mandelkow et al.

(10) Patent No.: US 6,579,691 B1
(45) Date of Patent: Jun. 17, 2003

(54) PROTEIN KINASE NPK-110

(75) Inventors: Eckhard Mandelkow, Hamburg (DE); Eva-Marie Mandelkow, Hamburg (DE); Jacek Biernat, Hamburg (DE); Gerard Drewes, Hamburg (DE)

(73) Assignee: Max-Planck-Gesellschaft zur Forderung der Wissenschaften, E.V., Munich (DE)

( * ) Notice: Subject to any disclaimer, the term of this patent is extended or adjusted under 35 U.S.C. 154(b) by 0 days.

(21) Appl. No.: 08/817,832

(22) PCT Filed: Oct. 30, 1995

(86) PCT No.: PCT/EP95/04258

§ 371 (c)(1), (2), (4) Date: Sep. 9, 1997

(87) PCT Pub. No.: WO96/13592

PCT Pub. Date: May 9, 1996

(30) Foreign Application Priority Data

Oct. 28, 1994 (EP) ............................................. 94117122

(51) Int. Cl.⁷ ............................. C12N 9/12; C12Q 1/48; A61K 38/45
(52) U.S. Cl. ........................ 435/15; 435/68.1; 435/194; 424/94.5
(58) Field of Search ............................... 435/194, 68.1, 435/15; 424/94.5

(56) References Cited

PUBLICATIONS

West, et al., "A model for microtubular–associated protein–4 structure: Domains defined by comparisons of human, mouse, and bovine sequences," *J.Biol.Chem.*, 266:21886–21896 (1991).

Wille, et al., "Alzheimer–like paired helical filaments and antiparallel dimers formed from microtubule–associated protein tau in vitro," *J.Cell Biol.*, 118:573–584 (1992).

Wischik, et al., "Isolation of a fragment of tau derived from the core of the paired helical filament of Alzheimer disease," *Proc.Nat'l.Acad.Sci.(USA)* 85:4506–4510 (1988).

Albala et al., "Characterization of the transcripts encoding 2 isoforms of human microtubule–associated protein–2 (MAP–2)," *Gene*, 136:377–378 (1993).

Anderton, "Expression and processing of pathological proteins in Alzheimer's disease," *Hippocampus*, 3:227–237 (1993).

Baas, et al., "Processes induced by tau expression in Sf9–cells have an axon–like microtubule organization," *J.Cell Biol.*, 115:1333–1344 (1991).

Baumann, et al., "Abnormal Alzheimer–like phosphorylation of tau protein by cyclin–dependent kinases cdk2 and cdk5," *FEBS Lett.*, 336:417–424 (1993).

Berling, et al., "Phosphorylation of microtubule–associated proteins MAP2a,b and MAP2c at serine 136 by proline–directed kinases in vivo and in vitro," *Eur.J.Cell Biol.*, 64:120–130 (1994).

Biernat, et al., "The switch of tau protein to an Alzheimer–like state includes the phosphorylation of two serine–proline motifs upstream of the microtubule binding region," *EMBO J.*, 11:1593–1597 (1992).

Biernat, et al., "Phosphorylation of serine 262 strongly reduces the binding of tau protein to microtubules: Distinction between PHF–like immunoreactivity and microtubule binding," *Neuron*, 11:153–163 (1993).

Boyle, et al., "Phosphopeptide mapping and phosphoamino acid analysis by two–dimensional separation on thin layer cellulose plate," *Methods Enzymol.*, 201:110–149 (1991).

Bramblett, et al., "Abnormal tau phosphorylation at Ser (396) in Alzheimer's disease recapitulates development and contributes to reduced microtubule binding," *Neuron*, 10:1089–1099 (1993).

Brandt, et al., "Functional organization of microtubule–associated protein tau: Identification of regions which affect microtubule growth, nucleation, and bundle formation in vitro," *J.Biol.Chem.*, 268:3414–3419 (1993).

Brion, et al., "A68 proteins in Alzheimers–disease are composed of several tau isoforms in a phosphorylated state which affects their electrophoretic mobilities," *Biochem.J.*, 279:831–836 (1991).

Brugg, et al., "Phosphorylation determines the binding of microtubule–associated protein–2 (MAP2) to microtubules in living cells," *J.Cell.Biol.*, 114:735–743 (1991).

Butler, et al., "Microheterogeneity of microtubule–associated tau–proteins is due to differences in phosphorylation," *J.Neurochem.*, 47:1517–1522 (1986).

Butner, et al., "Tau–protein binds to microtubules through a flexible array of distributed weak sites," *J.Cell Biol.*, 115:717–730 (1991).

Casnelli, et al., "Assay of protein kinases using peptides with basic residues for phosphocellulose binding," *Meth.Enzymology*, 200:115–120 (1991).

(List continued on next page.)

*Primary Examiner*—Rebecca E. Prouty
(74) *Attorney, Agent, or Firm*—Marshall, Gerstein & Borun

(57) ABSTRACT

The present invention relates to a DNA sequence encoding a neuronal protein kinase (NPK) which phosphorylates tau proteins as well as other microtubule associated proteins (MAPs) in positions crucial for the binding to microtubules. The invention further relates to Serine or Theorine residues and epitopes comprising said residues phosphorylated by said NMK on said MAPs, to antibodies specifically binding to said protein kinase, pharmaceutical compositions comprising inhibitors to said protein kinase, in particular for the treatment of Alzheimer's disease and cancer, to diagnostic kits and to in vitro diagnostic methods for the detection of Alzheimer's disease and cancer.

5 Claims, 17 Drawing Sheets

OTHER PUBLICATIONS

Figure 3:
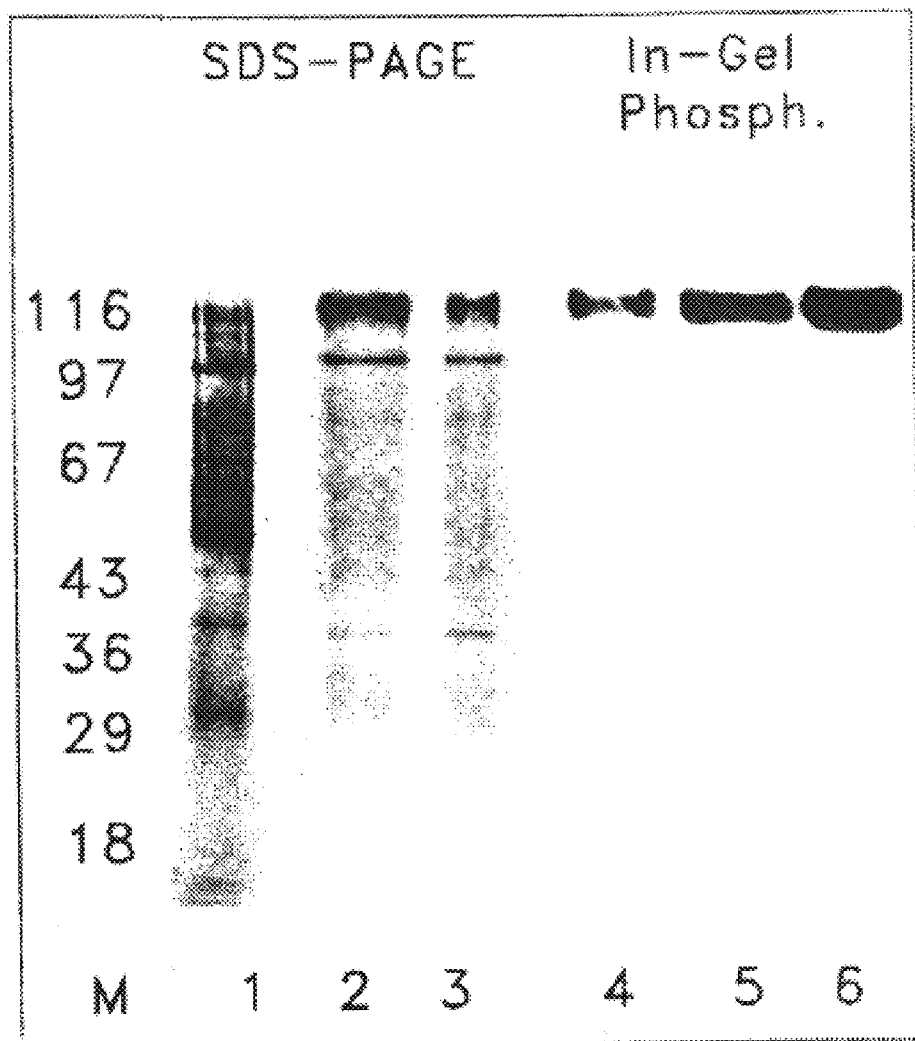

Chapin, et al., "Non–neuronal 210 kD Mn microtubule–associated protein (MAP4) contains a domain homologous to the microtubule–binding domains of neuronal MAP2 and tau," *J.Cell Sci.*, 98:27–36 (1991).

Chapin, et al., "Microtubule stabilization by assembly–promoting microtubule–associated proteins: A repeat performance," *Cell Mot.Cytoskel*, 23:236–243 (1992).

Chen, et al., "Projection domains of MAP2 and tau determine spacings between microtubules in dendrites and axons," *Nature*, 360:674–677 (1992).

Cleveland, et al., "Purification of tau, a microtubule–associated protein that induces assembly of microtubules from purified tubulin," *J.Mol.Biol.* 116:207–225 (1977).

Correas, et al., "Microtubule associated protein tau is phosphorylated by protein kinase C on its tubulin binding domain," *J.Biol.Chem.*, 267:15721–15728 (1992).

Drechsel, et al., "Modulation of the dynamic instability of tubulin assembly by the microtubule–associated protein tau," *Mol.Biol.Cell*, 3:1141–1154 (1992).

Drewes, et al., "Mitogen–activated protein (MAP) kinase transforms tau protein into an Alzheimer like state," *EMBO J.*, 11:2131–2138 (1992).

Drewes, et al., "Dephosphorylation of tau protein and Alzheimer paired helical filaments by calcineurin and phosphatase–2A," *FEBS Lett.*, 336:425–432 (1993).

Drubin, et al., "Tau protein function in living cells," *J.Cell Biol.* 103:2739–2746 (1986).

Ennulat, et al., "Two separate 18–amino acid domains of tau promote the polymerization of tubulin," *J.Biol.Chem.* 264:5327–5330 (1989).

Geahlen, et al., "Detection of protein kinase activity in sodium dodedyl sulfate–polyacrylamide gels," *Anal.Biochem.*, 153:151–158 (1986).

Goedert, et al., "Multiple isoforms of human microtubule–associated protein–tau: Sequences and localization in neurofibrillary tangles of Alzheimer–disease," *Neuron* 3:519–526 (1989).

Goedert, et al., "Tau proteins of Alzheimer paired helical filaments: Abnormal phosphorylation of all six brain isoforms," *Neuron*, 8:159–168 (1992).

Goedert, et al., "Tau protein and the neurofibrillary pathology of Alzheimer's disease," *Trends in Neurosci.*, 16:460–465 (1993).

Gong, et al., "Alzheimer's disease abnormally phosphorylated tau is dephosphorylated by protein phosphatase–2b (calcineurin)," *J.Neurochem.*, 62:803–806 (1994).

Goode, et al., "Identification of a novel microtubule binding and assembly domain in the developmentally regulated inter–repeat region of tau," *J.Cell Biol.*, 124:769–782 (1994).

Greenberg, et al., "Hydrofluoric acid–treated tau–PHF proteins display the same biochemical properties as normal tau," *J.Biol.Chem.*, 267:264–569 (1992).

Grundke–Igbal, et al., "Abnormal phosphorylation of the microtubule–associated protein tau in Alzheimer cytoskeletal pathology," *Proc.Nat'l.Acad.Sci.(USA)*, 83:4913–4917 (1986).

Gustke, et al., "The Alzheimer–like phosphorylation of tau protein reduces microtubule binding and involves Ser–Pro and Thr–Pro motifs," *FEBS Lett.*, 307:199–205 (1992).

Gustke, et al., "Domains of Tau Protein and Interactions with Microtubules," *Biochemistry*, 33:9511–9522 (1994).

Hagestedt, et al., "Tau protein becomes long and stiff upon phosphorylation: Correlation between paracrystalline structure and degree of phosphorylation," *J.Cell Biol.* 109:1643–1651 (1989).

Hanger, et al., "Glycogen–synthase kinase–3 induced Alzheimer's disease–like phosphorylation of tau: Generation of paired helical filament epitopes and neuronal localization of the kinase," *Neurosci.Lett.* 147:58–62 (1992).

Hanks, et al., "Protein–kinase catalytic domain sequence database: Identification of conserved features of primary structure and classification of family members," *Meth.Enzymol.*, 200:38–62 (1991).

Hasegawa, et al., "Protein sequence and mass spectrometric analyses of tau in the Alzheimer's disease brain," *J.Biol.Chem.*, 26:17047–17054 (1992).

Himmler, et al., "Tau consists of a set of proteins with repeated C–terminal microtubule–binding domains and variable N–terminal domains," *Mol.Cell Biol.*, 9:1381–1388 (1989).

Hirokawa, et al., "Microtubule organization and dynamics dependent on microtubule–associated proteins," *Curr.Opinion Cell Biol.* 6:74–81 (1994).

Hirs, et al., "Modification of cysteins residues," *Methods Enzymol.*, 11:325–329 (1967).

Inglis, et al., "Emk, a protein–kinase with homologs in yeast maps to mouse chromosome–19," *Mamm.Genome*, 4:401–403 (1993).

Ishiguro, et al., "A serine threonine proline kinase–activity is included in the tau–protein kinase fraction forming a paired helical filament epitope," *Neurosci. Lett.*, 128:195–198 (1991).

Joly, et al., "Peptides corresponding to the 2nd repeated sequence in map–2 inhibit binding of microtubule–associated proteins to microtubules," *Biochemistry*, 29:8916–8920 (1990).

Kanemaru, et al., Fetal–type phosphorylation of the tau in paired helical filaments, *J.Neurochem*, 58:1667–1675 (1992).

Kemp, et al., "Protein kinase recognition sequence motifs," *TIBS*, 15:342–346 (1990).

Kindler, et al., "Complete cDNA sequence encoding rat high and low molecular weight MAP2," *Nucl.Acids Res.*, 18:2822 (1990).

Kobayashi, et al., "A cdc2–related kinase pssalre/cdk5 is homologous with the 30 kDa subunit of tau protein kinase–ii, a proline–directed protein–kinase associated with microtubule," *FEBS Lett.*, 335:171–175 (1993).

Kondo, et al., "The carboxyl third of tau is tightly bound to paired helical filaments," *Neuron*, 1:827–834 (1988).

Ksiezak–Reading, et al., "Structural stability of paired helical filaments requires microtubule–binding domains of tau: A model for self–association," *Neuron*, 6:717–728 (1991).

Ksierzak–Reading, et al., "Phosphate analysis and dephosphorylation of modified tau associated with paired helical filaments," *Brain Res.*, 597:209–219 (1992).

Lang, et al., "Immunulogical and conformation characterization of a phosphorylated immunodominant epitope on the paired helical filaments found in Alzheimer's disease," *Biochem.Biophys.Res.Comm.*, 187:783–790 (1992).

Lee, et al., "The microtubule binding domain of tau–protein," *Science*, 251:675–678 (1991).

Lee, et al., "A68–a major subunit of paired helical filaments and derivatised forms of normal tau," *Science*, 251:675–678 (1991).

Lee, et al., "The disordered neuronal cytoskeleton in Alzheimer's disease," *Curr.Opin.Neurobiol.*, 2:653–656, (1992).

Lee, et al., "Expression of tau protein in non–neuronal cells: microtubule binding and stabilization," *J.Cell Sci.*, 102:227–237 (1992).

Lee, et al., "Non–motor microtubule–associated proteins," *Curr.Opin.Cell Biol.* 5:88–94 (1993).

Levin, et al., "A putative protein–kinase gene (kin1+) is important for growth polarity in Schizosaccharomyces pombe," *Proc.Nat'l.Acad.Sci.(USA)*, 87:8272–8276 (1990).

Levin, et al., "Two yeast genes that encode unusual protein kinases," *Proc.Nat'l.Acad.Sci.(USA)*, 84:6035–6039 (1987).

Lichtenberg–Kraag, et al., "Phosphorylation dependent interaction of neurofilament antibodies with tau protein: Epitopes, phosphorylation sites, and relationship with Alzheimer tau," *Proc.Nat'l.Acad.Sci.(USA)*, 89:5384–5388 (1992).

Mandelkow, et al., "Tubulin domains probed by sub-unit–specific antibodies and limited proteolysis," *J.Mol.Biol.*, 185:311–327 (1985).

Mandelkow, et al., "Glycogen synthase kinase–3 and the Alzheimer–like state of microtubule–associated protein tau," *FEBS Lett.*, 314:315–321 (1992).

Mandelkow, et al., "Tau as a marker for Alzheimer's disease," *TIBS* 18:480–483 (1993).

Mercken, et al., "Monoclonal antibodies with selective specificity for Alzheimer tau are directed against phosphatase–sensitive epitopes," *Acta Neuropathol.*, 84:265–272 (1992).

Meyer, et al., "Determination and location of phosphoserine in proteins and peptides by conversion to S–ethyl–cysteins," *Meth.Enzymol.*, 201:169–185 (1991).

Paudel, et al., "Brain proline–directed protein kinase phosphorylates tau on sites that are abnormally phosphorylated in tau associated with Alzheimer's paired helical filaments," *J.Biol.Chem.*, 268:23512–23518 (1993).

Schweers, et al., "Structural studies of tau protein and Alzheimer paired helical filaments show no evidence for β Structure," *J.Biol.Chem.*, 269:24290–24297 (1994).

Scott, et al., "Phosphorylation of recombinant tau by cAMP––dependent protein kinase: Identification of phosphorylation sites and effect on microtubule assembly," *J.Biol.Chem.*, 268:1166–1173 (1993).

Steiner, et al., "Phosphorylation of microtubule–associated protein tau: Identification of the site for $Ca^{++}$–calmodulin dependent kinase and relationship with tau phosphorylation in Alzheimer tangles," *EMBO J.*, 9:3539–3544 (1990).

Steiner, et al., "Phosphorylation of microtubule–associated protein tau and role in Alzheimer's disease," Ph.D. Thesis, University of Hamburg (1993).

Studier, et al., "Use of T7 RNA polymerase to direct the expression of cloned genes," *Meth.Enzym.*, 185:60–89 (1990).

Tarr, et al., Complete amino acid sequence and predicted membrane topology of phenobarbital–induced cytochrome P–450 isoenzyme 2 from rabbit liver microsomes, *Proc. Nat'l.Acad.Sci.(USA)*, 80:6552–6556 (1983).

Trinczek, et al., "Dynamics of microtubules from erythrocyte marginal bands," *Molec.Biol.Cell* 4:323–335 (1993).

Vulliet, et al., "Proline–directed phosphorylation of human tau protein," *J.Biol.Chem.*, 267:22570–22574 (1992).

Watanabe, et al., "In–vivo phosphorylation sites in fetal and adult rat tau," *J.Biol.Chem.*, 268:25712–25717 (1993).

htau40
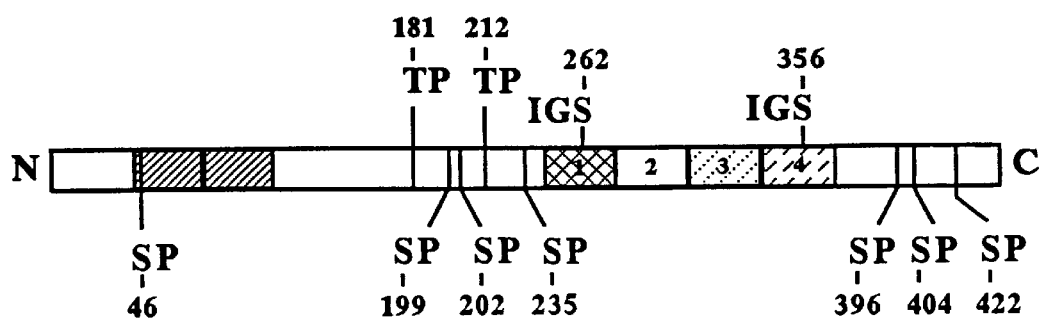
K18
Fig.1

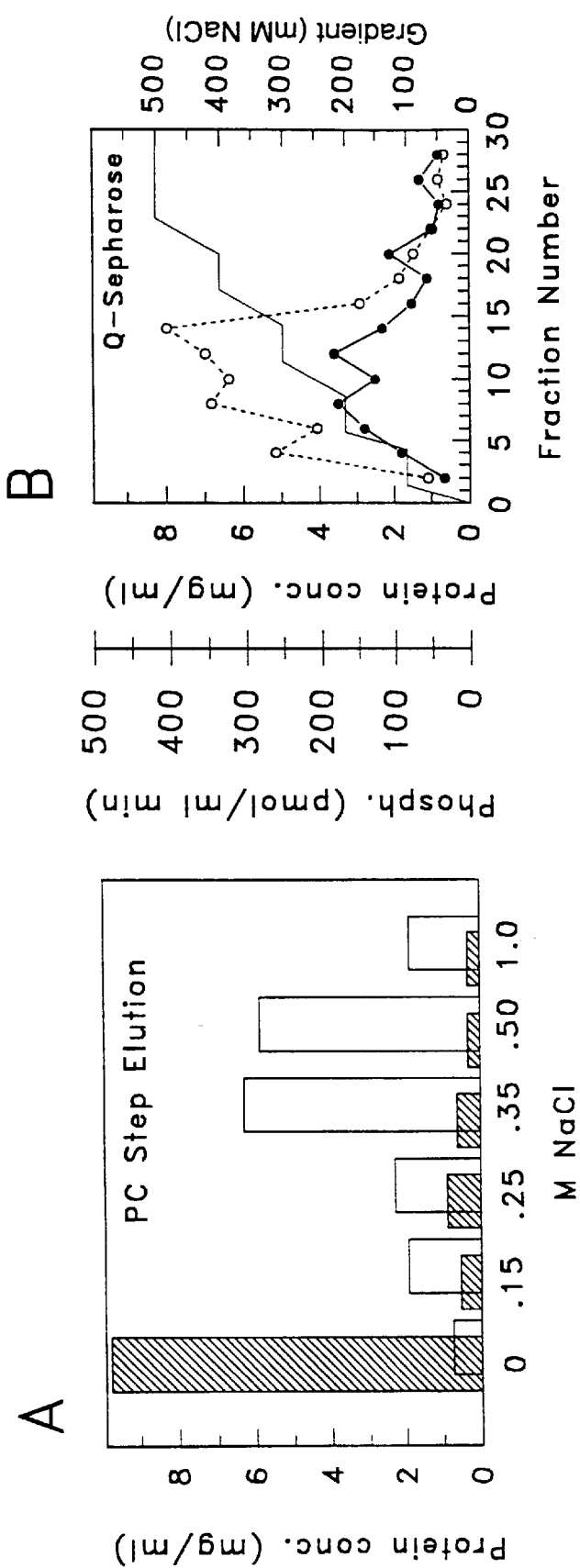
Fig. 2 A,B

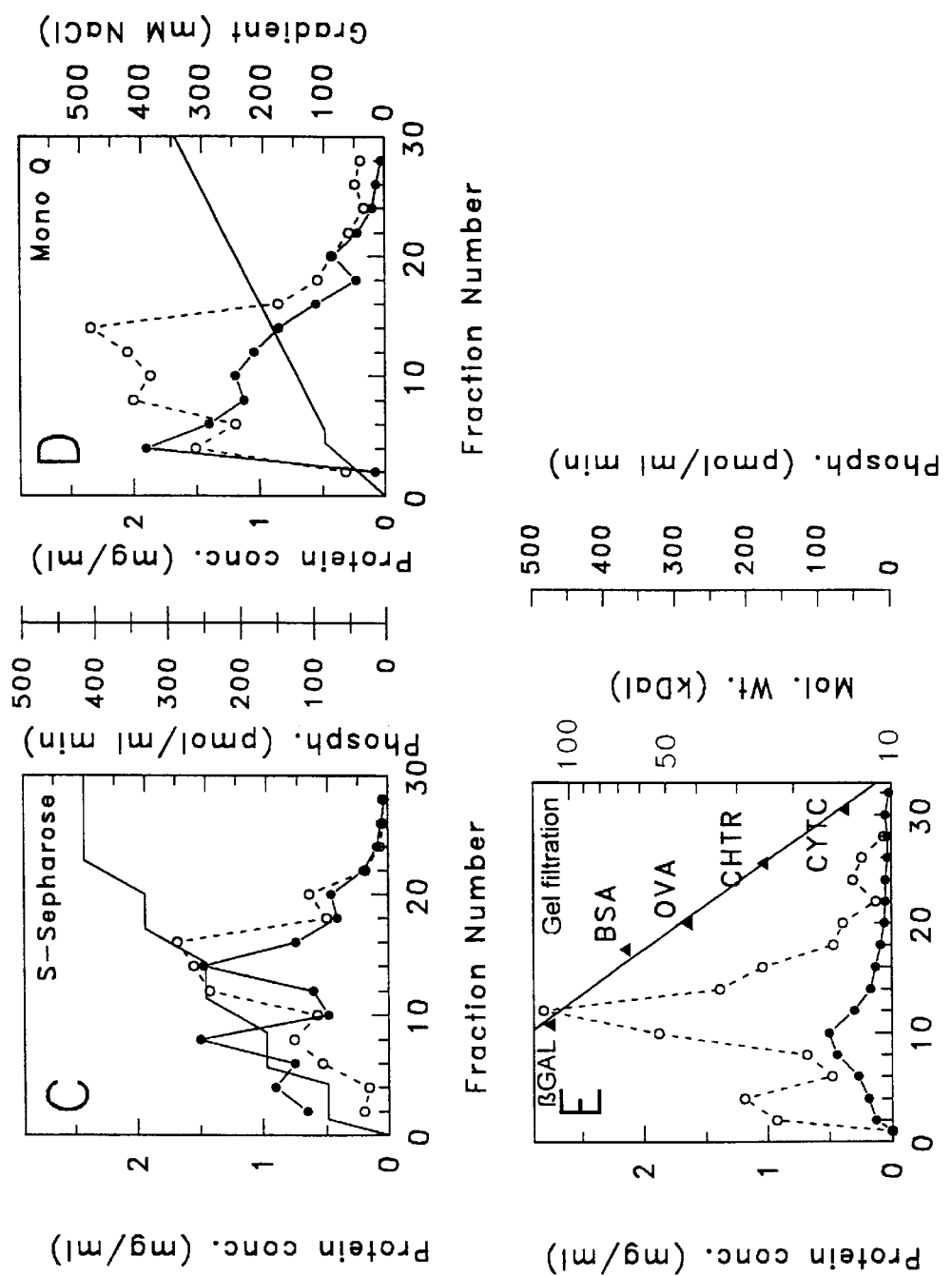
Fig. 2 C,D,E

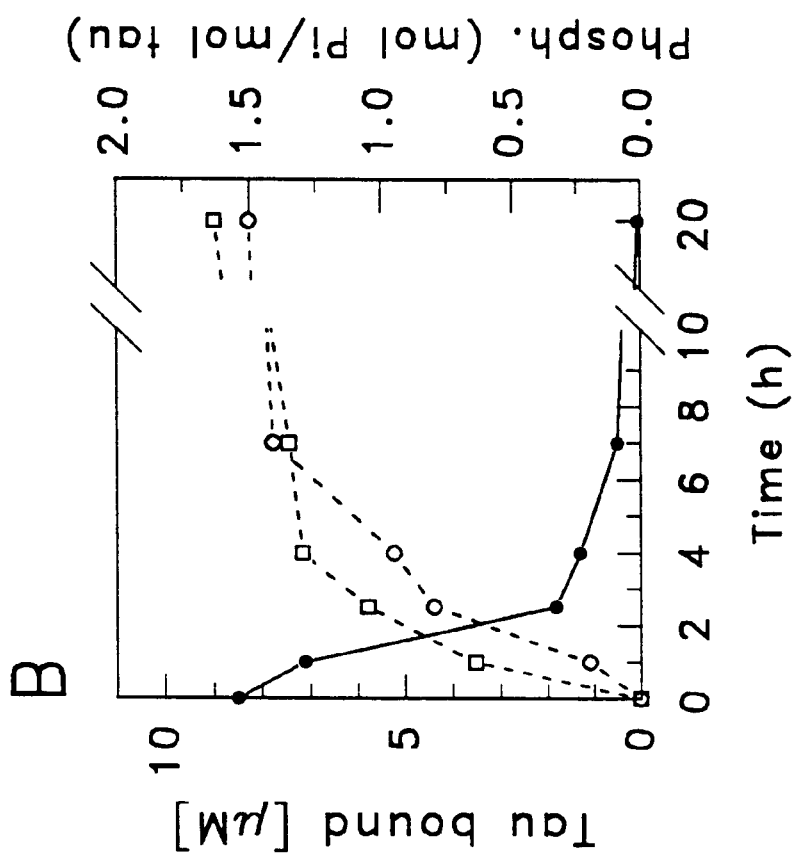
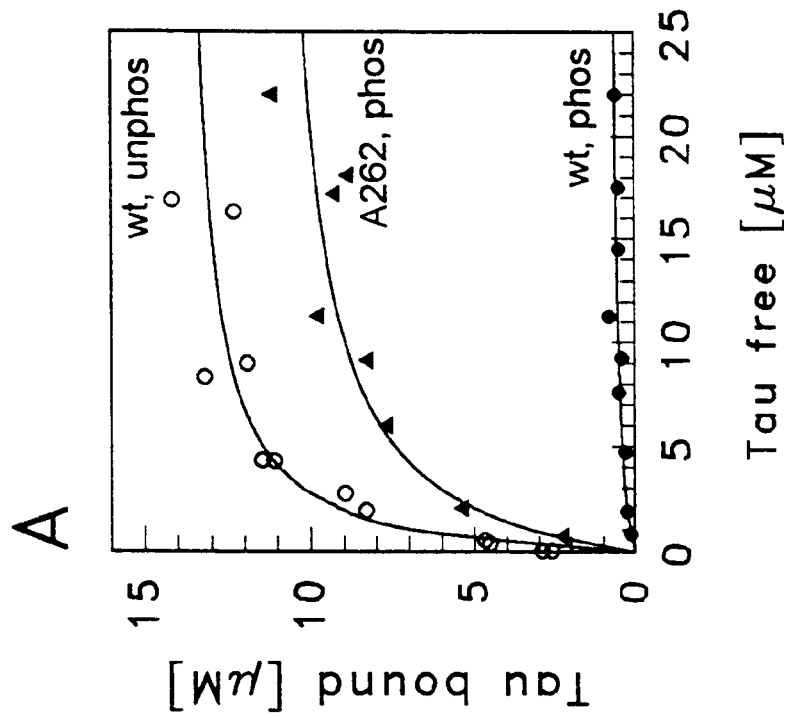
Fig. 6 a)
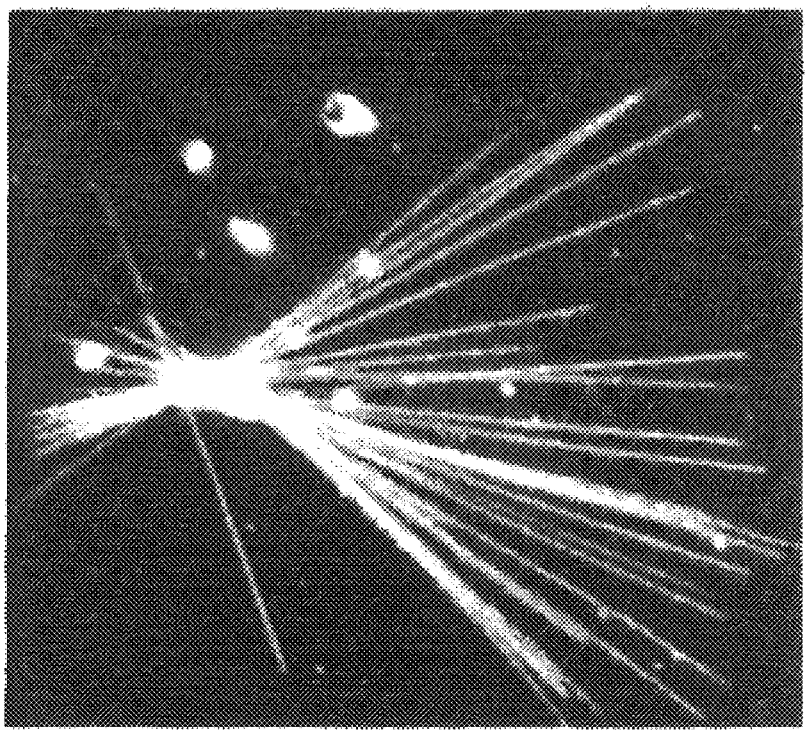
b)
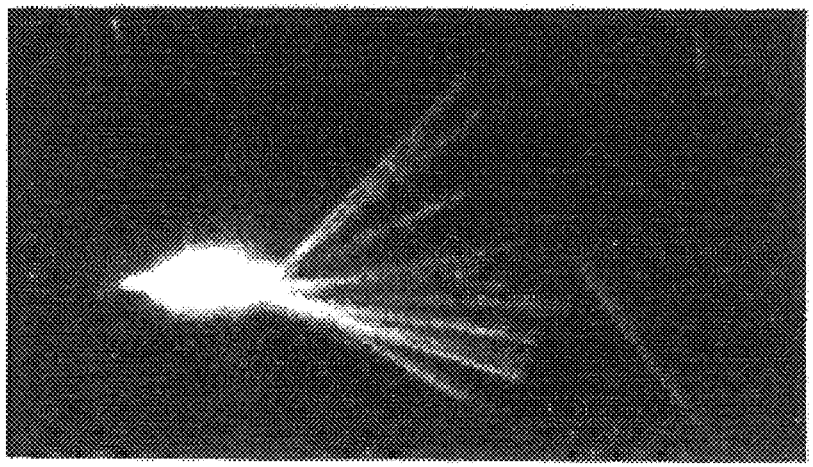
10 μm
Fig. 7

Effect of Ser262 Phosphorylation on microtubule binding

Phosphopeptide map of MAP4 Fusion protein phosphorylated by NPK110.

SEQUENCE LISTING (1) GENERAL INFORMATION:

(iii) NUMBER OF SEQUENCES: 32

-continued

```
(2) INFORMATION FOR SEQ ID NO: 1:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Lys Leu Asp Thr Phe Cys Gly Ser Pro Pro Tyr Ala Ala Pro Glu Leu
1               5                   10                  15

Phe Gln Gly Lys
            20

(2) INFORMATION FOR SEQ ID NO: 2:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Asp Arg Trp Met Asn Val Gly His Glu Glu Glu Leu Lys Pro Tyr
1               5                   10                  15

Ala Glu Pro (2) INFORMATION FOR SEQ ID NO: 3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Lys Ser Ser Arg Gln Asn Ile Pro Arg Cys Arg Asn Asn Ile
1               5                   10

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/note= "Ser at position 3 is
            phosphorylated."

(xi) SEQUENCE DESCRIPTION: SEQ ID NO: 4:

Ile Gly Ser Thr Glu Asn Leu Lys
1               5

(2) INFORMATION FOR SEQ ID NO: 5:
```

```
        (i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
            (D) OTHER INFORMATION:/note= "Ser at position 3 is
                phosphorylated."

(xi) SEQUENCE DESCRIPTION: SEQ ID NO: 5:

Ile Gly Ser Leu Asp Asn Ile Pro His Val Pro Gly Gly Gly Asn His
1               5                   10                  15

Lys (2) INFORMATION FOR SEQ ID NO: 6:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
            (D) OTHER INFORMATION:/note= "Ser at position 3 is
                phosphorylated."

(xi) SEQUENCE DESCRIPTION: SEQ ID NO: 6:

Cys Gly Ser Leu Gly Asn Ile His His Lys
1               5                   10

(2) INFORMATION FOR SEQ ID NO: 7:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:7
            (D) OTHER INFORMATION:/note= "Ser at position 7 is
                phosphorylated."

(xi) SEQUENCE DESCRIPTION: SEQ ID NO: 7:

His Val Pro Gly Gly Gly Ser Val Gln Ile Val Tyr Lys
1               5                   10

(2) INFORMATION FOR SEQ ID NO: 8:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
```

(D) OTHER INFORMATION:/note= "Ser at position 3 is
                phosphorylated."

(xi) SEQUENCE DESCRIPTION: SEQ ID NO: 8:

Cys Gly Ser Leu Lys
1               5

(2) INFORMATION FOR SEQ ID NO: 9:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:3
            (D) OTHER INFORMATION:/note= "Ser at position 3 is
                phosphorylated."

(xi) SEQUENCE DESCRIPTION: SEQ ID NO: 9:

Ile Gly Ser Thr Asp Asn Ile Lys
1               5

(2) INFORMATION FOR SEQ ID NO: 10:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:5
            (D) OTHER INFORMATION:/note= "Ser at position 5 is
                phosphorylated."

(xi) SEQUENCE DESCRIPTION: SEQ ID NO: 10:

Asp Gln Gly Gly Ser Gly Glu Gly Leu Ser Arg
1               5                   10

(2) INFORMATION FOR SEQ ID NO: 11:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:2
            (D) OTHER INFORMATION:/note= "Ser at position 2 is
                phosphorylated."

(xi) SEQUENCE DESCRIPTION: SEQ ID NO: 11:

Ser Ser Leu Pro Pro
1               5

(2) INFORMATION FOR SEQ ID NO: 12:

(i) SEQUENCE CHARACTERISTICS:
            (A) LENGTH: 11 amino acids

```
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:2
        (D) OTHER INFORMATION:/note= "Ser at position 2 is
            phosphorylated."

(ix) FEATURE:
        (A) NAME/KEY: Peptide
        (B) LOCATION:6
        (D) OTHER INFORMATION:/note= "Ser at position 6 is
            phosphorylated."

(ix) FEATURE:
        (A) NAME/KEY: Peptide
        (B) LOCATION:9
        (D) OTHER INFORMATION:/note= "Ser at position 9 is
            phosphorylated."

(xi) SEQUENCE DESCRIPTION: SEQ ID NO: 12:

Leu Ser Asn Val Ser Ser Ser Gly Ser Ile Asn
1               5                   10

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:5
        (D) OTHER INFORMATION:/note= "Thr at position 5 is
            phosphorylated."

(xi) SEQUENCE DESCRIPTION: SEQ ID NO: 13:

Ser Pro Ala Thr Thr Leu Pro
1               5

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/note= "Ser at position 3 is
            phosphorylated."

(xi) SEQUENCE DESCRIPTION: SEQ ID NO: 14:

Val Gly Ser Thr Glu Asn Ile Lys
1               5

(2) INFORMATION FOR SEQ ID NO: 15:

(i) SEQUENCE CHARACTERISTICS:
        (A) LENGTH: 11 amino acids
        (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Peptide
            (B) LOCATION:6
            (D) OTHER INFORMATION:/note= "Ser at position 6 is
                phosphorylated."

(xi) SEQUENCE DESCRIPTION: SEQ ID NO: 15:

Leu Ala Thr Thr Val Ser Ala Pro Asp Leu Lys
1               5                   10

(2) INFORMATION FOR SEQ ID NO: 16:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:2
            (D) OTHER INFORMATION:/note= "Thr at position 2 is
                phosphorylated."

(ix) FEATURE:
            (A) NAME/KEY: Peptide
            (B) LOCATION:3
            (D) OTHER INFORMATION:/note= "Thr at position 3 is
                phosphorylated."

(ix) FEATURE:
            (A) NAME/KEY: Peptide
            (B) LOCATION:5
            (D) OTHER INFORMATION:/note= "Thr at position 5 is
                phosphorylated."

(xi) SEQUENCE DESCRIPTION: SEQ ID NO: 16:

Asn Thr Thr Pro Thr Gly Ala Ala Pro Pro
1               5                   10

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:2
            (D) OTHER INFORMATION:/note= "Ser at position 2 is
                phosphorylated."

(ix) FEATURE:
            (A) NAME/KEY: Peptide
            (B) LOCATION:6
            (D) OTHER INFORMATION:/note= "Ser at position 6 is
                phosphorylated."

(xi) SEQUENCE DESCRIPTION: SEQ ID NO: 17:

Ser Ser Gly Ala Leu Ser Val Asp Lys
1               5
```

(2) INFORMATION FOR SEQ ID NO: 18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:3
        (D) OTHER INFORMATION:/note= "Ser at position 3 is
             phosphorylated."

(xi) SEQUENCE DESCRIPTION: SEQ ID NO: 18:

Val Gly Ser Leu Asp
1               5

(2) INFORMATION FOR SEQ ID NO: 19:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:6
        (D) OTHER INFORMATION:/note= "Ser at position 6 is
             phosphorylated."

(xi) SEQUENCE DESCRIPTION: SEQ ID NO: 19:

Leu Ala Thr Thr Val Ser Ala Pro Asp Leu Lys
1               5               10

(2) INFORMATION FOR SEQ ID NO: 20:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Asp Arg Trp Met Asn Val Gly His Glu Glu Glu Leu Lys Pro Tyr
1               5               10                  15

Ala Glu Pro Glu Pro
            20

(2) INFORMATION FOR SEQ ID NO: 21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Ile Ala Asn Glu Leu Lys
1               5

(2) INFORMATION FOR SEQ ID NO: 22:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Ala Glu Asn Leu Leu Leu Asp Ala Asp Met Asn Ile Lys
1               5                   10

(2) INFORMATION FOR SEQ ID NO: 23:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Xaa Ser Ser Arg Gln Asn Ile Pro Arg Cys Arg Asn Asn Ile Ile
1               5                   10                  15

(2) INFORMATION FOR SEQ ID NO: 24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Ile Leu Asn His Pro Asn Ile Val Lys
1               5

(2) INFORMATION FOR SEQ ID NO: 25:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Leu Asp Thr Phe Cys Gly Ser Pro Pro Tyr Ala Ala Pro Glu Leu Phe
1               5                   10                  15

Gln Gly Lys (2) INFORMATION FOR SEQ ID NO: 26:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Leu Phe Val Leu Asn Pro Ile Lys

```
1               5

(2) INFORMATION FOR SEQ ID NO: 27:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Leu Phe Arg Glu Val Arg Ile Xaa
1               5

(2) INFORMATION FOR SEQ ID NO: 28:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Tyr Arg Ile Pro Phe Tyr Met Ser Thr Asp Cys Glu Asn
1               5                   10

(2) INFORMATION FOR SEQ ID NO: 29:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Phe Arg Gln Ile Val Ser Ala Val Gln Tyr Cys His Gln Lys
1               5                   10

(2) INFORMATION FOR SEQ ID NO: 30:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Arg Ile Glu Ile Met Val Thr Met Gly Phe Leu
1               5                   10

(2) INFORMATION FOR SEQ ID NO: 31:

(i) SEQUENCE CHARACTERISTICS:
        (A) LENGTH: 779 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 31:
```

-continued

```
Thr Glu Asn His Thr Ser Val Asp Gly Tyr Thr Glu Thr His Ile Pro
1               5                   10                  15

Pro Thr Lys Ser Ser Ser Arg Gln Asn Ile Pro Arg Cys Arg Asn Ser
            20                  25                  30

Ile Thr Ser Ala Thr Asp Glu Gln Pro His Ile Gly Asn Tyr Arg Leu
            35                  40                  45

Gln Lys Thr Ile Gly Lys Gly Asn Phe Ala Lys Val Lys Leu Ala Arg
    50                  55                  60

His Val Leu Thr Gly Arg Glu Val Ala Val Lys Ile Ile Asp Lys Thr
65                  70                  75                  80

Gln Leu Asn Pro Thr Ser Leu Gln Lys Leu Phe Arg Glu Val Arg Ile
                85                  90                  95

Met Lys Ile Leu Asn His Pro Asn Ile Val Lys Leu Phe Glu Val Ile
            100                 105                 110

Glu Thr Glu Lys Thr Leu Tyr Leu Val Met Glu Tyr Ala Ser Gly Gly
            115                 120                 125

Glu Val Phe Asp Tyr Leu Val Ala His Gly Arg Met Lys Glu Lys Glu
            130                 135                 140

Ala Arg Ala Lys Phe Arg Gln Ile Val Ser Ala Val Gln Tyr Cys His
145                 150                 155                 160

Gln Lys Cys Ile Val His Arg Asp Leu Lys Ala Glu Asn Leu Leu Leu
                165                 170                 175

Asp Ala Asp Met Asn Ile Lys Ile Ala Asp Phe Gly Phe Ser Asn Glu
            180                 185                 190

Phe Thr Val Gly Asn Lys Leu Asp Thr Phe Cys Gly Ser Pro Pro Tyr
            195                 200                 205

Ala Ala Pro Glu Leu Phe Gln Gly Lys Lys Tyr Asp Gly Pro Glu Val
    210                 215                 220

Asp Val Trp Ser Leu Gly Val Ile Leu Tyr Thr Leu Val Ser Gly Ser
225                 230                 235                 240

Leu Pro Phe Asp Gly Gln Asn Leu Lys Glu Leu Arg Glu Arg Ser Cys
                245                 250                 255

Leu Arg Gly Lys Tyr Arg Val Pro Phe Tyr Met Ser Thr Asp Cys Glu
            260                 265                 270

Asn Leu Leu Lys Lys Leu Leu Val Leu Asn Pro Ile Lys Arg Gly Ser
            275                 280                 285

Leu Glu Gln Ile Met Lys Asp Arg Trp Met Asn Val Gly His Glu Glu
    290                 295                 300

Glu Glu Leu Lys Pro Tyr Ser Glu Pro Glu Leu Asp Leu Asn Asp Ala
305                 310                 315                 320

Lys Arg Ile Asp Ile Met Val Thr Met Gly Phe Ala Arg Asp Glu Ile
                325                 330                 335

Asn Asp Ala Leu Val Ser Gln Lys Tyr Asp Glu Val Met Ala Thr Tyr
            340                 345                 350

Ile Leu Leu Gly Arg Lys Pro Pro Glu Phe Glu Gly Gly Glu Ser Leu
            355                 360                 365

Ser Ser Gly Asn Leu Cys Gln Arg Ser Arg Pro Ser Ser Asp Leu Asn
    370                 375                 380

Asn Ser Thr Leu Gln Ser Pro Ala His Leu Lys Val Gln Arg Thr Ile
385                 390                 395                 400

Ser Ala Asn Gln Lys Gln Arg Arg Phe Ser Asp His Ala Gly Pro Ser
                405                 410                 415

Ile Pro Pro Ala Val Ser Tyr Thr Lys Arg Pro Gln Ala Asn Ser Val
```

```
                420               425               430
Glu Ser Glu Gln Lys Glu Glu Trp Asp Lys Asp Thr Ala Arg Arg Arg
            435               440               445
Gly Ser Thr Thr Val Gly Ser Lys Ser Glu Val Thr Ala Ser Pro Leu
450               455               460
Val Gly Pro Asp Arg Lys Lys Ser Ser Ala Gly Pro Ser Asn Asn Val
465               470               475               480
Tyr Ser Gly Gly Ser Met Thr Arg Arg Asn Thr Tyr Val Cys Glu Arg
                485               490               495
Ser Thr Asp Arg Tyr Ala Ala Leu Gln Asn Gly Arg Asp Ser Ser Leu
            500               505               510
Thr Glu Met Ser Ala Ser Ser Met Ser Ser Thr Gly Ser Thr Val Ala
            515               520               525
Ser Ala Gly Pro Ser Ala Arg Pro Arg His Gln Lys Ser Met Ser Thr
530               535               540
Ser Gly His Pro Ile Lys Val Thr Leu Pro Thr Ile Lys Asp Gly Ser
545               550               555               560
Glu Ala Tyr Arg Pro Gly Thr Ala Gln Arg Val Pro Ala Ala Ser Pro
                565               570               575
Ser Ala His Ser Ile Ser Ala Ser Thr Pro Asp Arg Thr Arg Phe Pro
            580               585               590
Arg Gly Ser Ser Arg Ser Thr Phe His Gly Glu Gln Leu Arg Glu
            595               600               605
Arg Arg Ser Ala Ala Tyr Ser Gly Pro Pro Ala Ser Pro Ser His Asp
            610               615               620
Thr Ala Leu Ala His Ala Arg Arg Gly Thr Ser Thr Gly Ile Ile
625               630               635               640
Ser Lys Ile Thr Ser Lys Phe Val Arg Arg Asp Pro Ser Glu Gly Glu
            645               650               655
Ala Ser Gly Arg Thr Asp Thr Ala Arg Gly Ser Ser Gly Glu Pro Lys
            660               665               670
Asp Lys Glu Glu Gly Lys Glu Ala Lys Pro Arg Leu Arg Phe Thr Trp
            675               680               685
Ser Met Lys Thr Thr Ser Ser Met Asp Pro Asn Asp Met Val Arg Glu
690               695               700
Ile Arg Lys Val Leu Asp Ala Asn Thr Cys Asp Tyr Glu Gln Arg Glu
705               710               715               720
Arg Phe Leu Leu Phe Cys Val His Gly Asp Ala Arg Gln Asp Ser Leu
            725               730               735
Val Gln Trp Glu Met Glu Val Cys Lys Leu Pro Arg Leu Ser Leu Asn
            740               745               750
Gly Val Arg Phe Lys Arg Ile Ser Gly Thr Ser Ile Ala Phe Lys Asn
            755               760               765
Ile Ala Ser Lys Ile Ala Asn Glu Leu Lys Leu
770               775
```

(2) INFORMATION FOR SEQ ID NO: 32:

(i) SEQUENCE CHARACTERISTICS:
        (A) LENGTH: 722 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

```
Met Ser Ser Ala Arg Thr Pro Leu Pro Thr Leu Asn Glu Arg Asp Thr
1               5                   10                  15

Glu Gln Pro Thr Leu Gly His Leu Asp Ser Lys Pro Ser Ser Lys Ser
            20                  25                  30

Asn Met Leu Arg Gly Arg Asn Ser Ala Thr Ser Ala Asp Glu Gln Pro
        35                  40                  45

His Ile Gly Asn Tyr Arg Leu Leu Lys Thr Ile Gly Lys Gly Asn Phe
    50                  55                  60

Ala Lys Val Lys Leu Ala Arg His Ile Leu Thr Gly Lys Glu Val Ala
65                  70                  75                  80

Val Lys Ile Ile Asp Lys Thr Gln Leu Asn Ser Ser Ser Leu Gln Lys
                85                  90                  95

Leu Phe Arg Glu Val Arg Ile Met Lys Val Leu Asn His Pro Asn Ile
            100                 105                 110

Val Lys Leu Phe Glu Val Ile Glu Thr Glu Lys Thr Leu Tyr Leu Val
        115                 120                 125

Met Glu Tyr Ala Ser Gly Gly Glu Val Phe Asp Tyr Leu Val Ala His
    130                 135                 140

Gly Arg Met Lys Glu Lys Glu Ala Arg Ala Lys Phe Arg Gln Ile Val
145                 150                 155                 160

Ser Ala Val Gln Tyr Cys His His Lys Phe Ile Val His Arg Asp Leu
                165                 170                 175

Lys Ala Glu Asn Leu Leu Leu Asp Ala Asp Met Asn Ile Lys Ile Ala
            180                 185                 190

Asp Phe Gly Phe Ser Asn Glu Phe Thr Phe Gly Asn Lys Leu Asp Thr
        195                 200                 205

Phe Cys Gly Ser Pro Pro Tyr Ala Ala Pro Glu Leu Phe Gln Gly Lys
210                 215                 220

Lys Tyr Asp Gly Pro Glu Val Asp Val Trp Ser Leu Gly Val Ile Leu
225                 230                 235                 240

Tyr Thr Leu Val Ser Gly Ser Leu Pro Phe Asp Gly Gln Asn Leu Lys
                245                 250                 255

Glu Leu Arg Glu Arg Val Leu Arg Gly Lys Tyr Arg Ile Pro Phe Tyr
            260                 265                 270

Met Ser Thr Asp Cys Glu Asn Leu Leu Lys Lys Phe Leu Ile Leu Asn
        275                 280                 285

Pro Ser Lys Arg Gly Thr Leu Glu Gln Ile Met Lys Asp Arg Trp Met
290                 295                 300

Asn Val Gly His Glu Asp Asp Glu Leu Lys Pro Tyr Val Glu Pro Leu
305                 310                 315                 320

Pro Asp Tyr Lys Asp Pro Arg Arg Thr Glu Leu Met Val Ser Met Gly
                325                 330                 335

Tyr Thr Arg Glu Glu Ile Gln Asp Ser Leu Val Gly Gln Arg Tyr Asn
            340                 345                 350

Glu Val Met Ala Thr Tyr Leu Leu Leu Gly Tyr Lys Ser Ser Glu Leu
        355                 360                 365

Glu Gly Asp Thr Ile Thr Leu Lys Pro Arg Pro Ser Ala Asp Leu Thr
370                 375                 380

Asn Ser Ser Ala Pro Ser Pro Ser His Lys Val Gln Arg Ser Val Ser
385                 390                 395                 400

Ala Asn Pro Lys Gln Arg Arg Ser Ser Asp Gln Ala Val Pro Ala Ile
                405                 410                 415
```

-continued

```
Pro Thr Ser Asn Ser Tyr Ser Lys Lys Thr Gln Ser Asn Asn Ala Glu
            420                 425                 430

Asn Lys Arg Pro Glu Glu Glu Thr Gly Arg Lys Ala Ser Ser Thr Ala
        435                 440                 445

Lys Val Pro Ala Ser Pro Leu Pro Gly Leu Asp Arg Lys Lys Thr Thr
    450                 455                 460

Pro Thr Pro Ser Thr Asn Ser Val Leu Ser Thr Ser Thr Asn Arg Ser
465                 470                 475                 480

Arg Asn Ser Pro Leu Leu Asp Arg Ala Ser Leu Gly Gln Ala Ser Ile
            485                 490                 495

Gln Asn Gly Lys Asp Ser Thr Ala Pro Gln Arg Val Pro Val Ala Ser
            500                 505                 510

Pro Ser Ala His Asn Ile Ser Ser Ser Gly Ala Pro Asp Arg Thr
            515                 520                 525

Asn Phe Pro Arg Gly Val Ser Ser Arg Ser Thr Phe His Ala Gly Gln
530                 535                 540

Leu Arg Gln Val Arg Asp Gln Gln Asn Leu Pro Phe Gly Val Thr Pro
545                 550                 555                 560

Ala Ser Pro Ser Gly His Ser Gln Gly Arg Arg Gly Pro Ser Gly Ser
            565                 570                 575

Ile Phe Ser Lys Phe Thr Ser Lys Phe Val Arg Arg Asn Leu Asn Glu
            580                 585                 590

Pro Glu Ser Lys Asp Arg Val Glu Thr Leu Arg Pro His Val Val Gly
            595                 600                 605

Gly Gly Gly Thr Asp Lys Glu Lys Glu Glu Phe Arg Glu Ala Lys Pro
            610                 615                 620

Arg Ser Leu Arg Phe Thr Trp Ser Met Lys Thr Thr Ser Ser Met Glu
625                 630                 635                 640

Pro Asn Glu Met Met Arg Glu Ile Arg Lys Val Leu Asp Ala Asn Ser
                645                 650                 655

Cys Gln Ser Glu Leu His Glu Arg Tyr Met Leu Leu Cys Val His Gly
            660                 665                 670

Thr Pro Gly His Glu Asn Phe Val Gln Trp Glu Met Glu Val Cys Lys
            675                 680                 685

Leu Pro Arg Leu Ser Leu Asn Gly Val Arg Phe Lys Arg Ile Ser Gly
    690                 695                 700

Thr Ser Met Ala Phe Lys Asn Ile Ala Ser Lys Ile Ala Asn Glu Leu
705                 710                 715                 720

Lys Leu
```

PROTEIN KINASE NPK-110

The present invention relates to a DNA sequence encoding a novel neuronal protein kinase (NPK) which phosphorylates tau proteins as well as other microtubule associated proteins (MAPs) in positions crucial for the binding to microtubules. The invention further relates to Serine or Theorine residues and epitopes comprising said residues phosphorylated by said NPK on said MAPs, to antibodies specifically binding to said protein kinase, pharmaceutical compositions comprising inhibitors to said protein kinase, in particular for the treatment of Alzheimer's disease and cancer, to diagnostic kits and to in vitro diagnostic methods for the detection of Alzheimer's disease and cancer.

Microtubule associated proteins (MAPs) regulate the extensive dynamics and rearrangement of the microtubule network which is thought to drive neurite outgrowth (reviewed recently by Hirokawa, 1994). Several lines of evidence suggest that the phosphodrylation state of MAPs, balanced by protein kinases and phosphatases in a hitherto unknown way, plays a pivotal role in the modulation of these events. Tau protein, a class of MAPs in mammalian brain (Cleveland et al., 1977), is phosphorylated on several sites in vivo (Butler & Shelanski 1986; Watanabe et al., 1993) and is a substrate for many protein kinases in vitro (reviewed by Lee, 1993; Goedert, 1993; Mandelkow & Mandelkow, 1993; Anderton, 1993). During neuronal degeneration in Alzheimer's disease, tau protein aggregates into paired helical filaments (PHFs), the principal fibrous component of the characteristic neurofibrillary lesions (reviewed by Lee & Trojanowski, 1992). Tau isolated from these aggregates displays some biochemical alterations, of which hyperphosphorylation is the most striking (Grundke-Iqbal et al., 1986; Brion et al., 1991; Ksiezak-Reding et al., 1992; Goedert et al., 1992). Most of the reported aberrant phosphorylation sites are Ser/Thr-Pro sequences (Lee et al., 1991; Biernat et al., 1992; Lichtenberg-Kraag et al., 1992; Gustke et al., 1992; Watanabe et al., 1993), suggesting a dysregulation of proline-directed kinases (Drewes et al., 1992; Mandelkow et al., 1992; Hanger et al., 1992; Vulliet et al., 1992; Baumann et al., 1993; Paudel et al., 1993, Kobayashi et al., 1993) or the corresponding phosphatases (Drewes et al., 1993; Gong et al., 1994). Phosphorylation-dependent antibodies, which discriminate between 'normal' tau and the hyperphosphorylated, 'pathological' forms, were prepared by several laboratories (Kondo et al., 1988; Lee et al., 1991; Mercken et al., 1992; Greenberg et al., 1992). All of these antibodies were shown to be directed against epitopes of the Ser/Thr-Pro type (Lee et al., 1991; Biernat et al., 1992; Lichtenberg-Kraag et al., 1992; Lang et al., 1992; Watanabe et al., 1993).

The microtubule binding region of tau (FIG. 1) includes three or four pseudorepeats of 31 residues each depending on isoform type (Lee et al., 1989; Goedert et al., 1989; Himmler et al., 1989). This region probably forms the building block of the paired helical filaments (Kondo et al., 1988; Wischik et al., 1988; Ksiezak-Reding & Yen, 1991; Wille et al., 1992). It does not contain any of the 14–16 Ser/Thr-Pro motifs, which accumulate in the regions flanking the repeats. However, it contains a conserved Serine residue (Ser262) within the sequence KIGS in the first repeat, which was found to be one of the predominant sites phosphorylated by a tissue extract from brain (Gustke et al., 1992). This site is also found to be phosphorylated in Alzheimer PHF-tau, but not in 'normal' tau or fetal tau (Hasegawa et al., 1992). So far, it is the only pathological phosphorylation site found within the repeat domain of tau. Recently, a site-directed mutagenesis approach was used to show that phosphorylation of tau at this site strongly decreases its microtubule binding capacity, whereas the phosphorylation on Ser/Thr-Pro motifs had only a minor effect (Biernat et al., 1993). This initiated a search for protein kinases in neuronal tissue with the ability to phosphorylate tau at Ser262. The technical problem underlying the present invention was to provide a protein kinase which is causative for the onset of Alzheimer's disease by phosphorylating the crucial Serine 262 residue of human tau protein and a corresponding nucleotide sequence.

The solution to this technical problem is achieved by providing the embodiments characterised in the claims.

Thus, the present: invention relates to a DNA sequence encoding a neuronal protein kinase (NPK) or a functional fragment thereof that is capable of phosphorylating a sequence motive of the type KXGS in tau, MAP4, MAP2 and MAP2c characterised by the following features:

(a) it encodes the amino acid sequence depicted as MARK-1 in Table 6;

(b) it encodes the amino acid sequence depicted as MARK-2 in Table 6; or (c) it hybridises to the DNA of (a) or (b).

The term "DNA sequence" comprises any DNA sequence such as genomic or cDNA, semisynthetic or synthetic DNA.

It was surprisingly found that none of the prior art kinases is mediating the phosphorylation of the four KXGS motifs in the repeat domain of tau to an extent that is sufficient to explain the biological and pathological effects associated with said phosphorylation. This is particularly true for Serine residue 262 which is indicative of the onset of Alzheimer's disease. Instead, the present invention provides a DNA sequence encoding a novel protein kinase with the above identified features which is responsible for the phosphorylation of the amino acid residues crucial for the onset of Alzheimer's disease. Said protein kinase is, also termed NPK, MARK-1 or MARK-2 throughout this application. The numbering of amino acid residues referred to in this application ensues with regard to the sequence of htau 40, the longest of the human tau isoforms (441 residues, Goedert et al., 1989).

In a preferred embodiment, the present invention further relates to a DNA sequence wherein the neuronal protein kinase (NPK) is characterised by the following features:

(a) it has an apparent molecular weight of 110 kD as determined by SDS-PAGE;

(b) it phosphorylates Serine residues 262, 293, 305, 324 and 356 of human tau protein; and (c) it comprises the following amino acid sequences
KLDTFCGSPPYAAPELFQGK (SEQ ID NO: 1)
DRWMNVGHEEEELKPYAEP (SEQ ID NO: 2)
(K) SSRQNIPRCRNNI (SEQ ID NO: 3)

In a preferred embodiment of the DNA sequence of the present invention, the NPK is further characterised by the following features:

(d) it is deactivated by phosphatase PP-2A; and (e) it phosphorylates the following Serine or Threonine residues of tau related microtubule-associated proteins (MAPs) MAP2, MAP2c and MAP4
MAP2/MAP2C: S37, S1536, S1676, S1707, S1792, S1796, S1799
MAP4: T829, T873, T874, T876, S899, S903, S928, S941, S1073

(f) it causes the dissociation of tau, MAP4, MAP2 and MAP2c from microtubules.

Another surprising finding that was made in accordance with the present invention is that the NPK by phosphorylating microtubule-associated proteins other than tau causes dissociation of these proteins from microtubules. This in turn results in the destabilisation of said microtubules, an increased dynamic instability thereof, and the ensuing effects on cell proliferation, cell differentiation, or cell degeneration. The NPK of the invention thus has the capacity to regulate the dynamics and rearrangements of microtubules in brain via the phosphorylation of tau or other MAPs. The finding referred to above has important implications for the role in the kinase of the invention in the generation of cancer.

This is because it is believed that cancer essentially is uncontrolled cell proliferation. Many anti-cancer drugs therefore interfere with cellular division and proliferation by poisoning the microtubules. On the other hand, "oncogenes" are often kinases, the cellular regulation of which is impaired. The deregulation of a kinase equal or homologous to the NPK of the invention could have serious effects on the stability of microtubules of various cell types. As microtubules play an important role in cell division, deregulation of said NPK can in turn lead to an uncontrolled cellular division and the transformation of normal cells to cancer cells. Alternatively, the deregulation of said NPK could provide postmitotic terminally differentiated cells such as neurons (which do not divide) with a stimulus to divide. This "unnormal" stimulus would lead the neurons directly into apoptosis (and thus, an Alzheimer's like state) because due to their differentiation status they are unable to divide.

In a further preferred embodiment of the DNA sequence of the present invention, the NPK is obtainable from brain tissue by the following steps:

(a) homogenisation of brain extract and subsequent centrifugation thereof;

(b) chromatography of the supernatant obtained in step (a) on cellulosephosphate, wherein the NPK active fractions elute between 200 to 400 mM NaCl;

(c) ammonium sulfate precipitation of active fractions obtained in step (b) and dialysis of the precipitate;

(d) anion exchange chromatography of the dialysate obtained in step (c) on Q-Sepharose (Pharmacia) and elution of the NPK active fractions, wherein said NPK active fractions elute as a single peak at about 0.2 M NaCl, with subsequent dialysis of the active fractions;

(e) cation exchange chromatography on Mono S HR 10/10 (Pharmacia);

(f) chromatography on Mono Q HR 5/5, wherein the NPK active fractions elute at about 250 mM NaCl;

(g) gel filtration chromatography on Superdex G-200, wherein the NPK activity elutes with an apparent molecular weight of 100 kD; and (h) affinity chromatography on ATP-cellulose, wherein the NPK active fractions elute with an apparent molecular weight of about 110 kD as determined by SDS-PAGE; wherein the NPK activity is measured by incubating a peptide comprising amino acid residues 255 to 267 of human adult tau in the presence of radioactively labelled ATP and determining the radioactivity incorporated into said peptide.

Further details as to how this NPK of the invention which in one embodiment has an apparent molecular weight of 110 kD (NPK-110) can be isolated are provided in Example 1. However, the person skilled in the art would know from the technical teaching given above how to supplement said details.

The NPK of the invention may be derived from any vertebrate brain. In a preferred embodiment, the NPK is derived from a mammalian brain.

The invention also relates to a RNA sequence complementary to the DNA sequence of the invention.

In a particularly preferred embodiment, said mammalian brain is human or porcine brain.

The invention further relates to a polypeptide encoded by the DNA sequence .or a functional fragment or derivative thereof. Said polypeptide, fragment or derivative may be posttranslationally or chemically modified. Throughout this specification, the term NPK or, alternatively, MARK (1 or 2) may also comprise such fragments or derivatives, even if this is not specifically indicated.

The present invention further relates to the following Serine or Threonine residues phosphorylated by NPK-110 of tau related microtubule-associated proteins (MAPs) MAP2, MAP2c and MAP4:

MAP2/MAP2c: S37, S1536, S1676, S1707, S1792, S1796, S1799

MAP4: T829, T873, T874, T876, S899, S903, S928, S941, S1073 and to epitopes comprising said phosphorylated Serine or Threonine residues.

The invention relates further to an antibody specifically binding to the NPK of the invention.

Said antibody may be a serum derived or a monoclonal, antibody. The production of both monoclonal and polyclonal antibodies to a desired epitope is well known in the art (see, for example, Harlow and Lane, Antibodies, A Laboratory Manual, Cold Spring Harbor Laboratory, Cold Spring Harbor, 1988). Furthermore, said antibody may be a natural or an antibody derived by genetic engineering, such as a chimeric antibody derived by techniques which are well understood in the art. Moreover, the term antibody as used herein also refers to a fragment of an antibody which has retained its capacity to bind the specific epitope, such as a Fab, F(ab)$_2$ or an Fv fragment.

Additionally, the present invention relates to an antibody specifically binding to epitopes comprising the phosphorylated Serine or Threonine residues of MAP2, MAP2c and MAP4:

MAP2/MAP2c: S37, S1536, S1676, S1707, S1792, S1796, S1799

MAP4: T829, T873, T874, T876, S899, S903, S928, S941, S1073

Again, said antibody may be a polyclonal or a monoclonal antibody, or a fragment thereof retaining its binding specificity.

In a preferred embodiment, the antibody of the invention is a monoclonal antibody or a fragment or derivative thereof.

In a further preferred embodiment of the invention, said antibody is a polyclonal antibody or a fragment or a derivative thereof.

The invention furthermore relates to a pharmaceutical composition which contains a specific inhibitor of the NPK of the invention, optionally in combination with a pharmaceutically acceptable carrier and/or diluent.

The term "specific inhibitor of the NPK of the invention" refers to substances which specifically inhibit the enzymatic action of the protein kinase of the present invention. Inhibitors to enzymes such as protein kinases and their mode of action are well known in the art. For example, such an inhibitor may bind to the catalytic domain of the enzyme, thus rendering it incapable of converting its substrate.

Said pharmaceutical composition may be administered to a patient in need thereof by a route and in a dosage which is deemed appropriate by the physician familiar with the case. Pharmaceutically acceptable carriers and/or diluents are well known in the art, and may be formulated according to the route of administration or the special disease status of the patient.

In a preferred embodiment, the present invention relates to a pharmaceutical composition for the treatment of Alzheimer's disease.

Again, said pharmaceutical composition may be administered to a patient in need thereof by a route and in a dosage which is deemed appropriate by the physician handling the case.

In a further preferred embodiment, the pharmaceutical composition of the present invention is used for the treatment of cancer.

As has been pointed out above, the deregulation of the NPK of the invention can lead a variety of cell types expressing microtubule associated proteins into a pathway that eventually results in the neoplastic transformation of said cells. Accordingly, a pharmaceutically effective amount of an NPK inhibitor will halt and/or reverse the transformation process. The amount of inhibitor to be administered will be determined by the physician handling the respective cases.

In a further preferred embodiment of the pharmaceutical composition of the invention, said inhibitor is the antibody of the invention, a phosphatase capable of dephosphorylating the NPK of the invention, preferably phosphatase PP-2A, an inhibitor of the activating kinase of said NPK, a tau derived peptide comprising the Ser262 residue or a MAP2, 2c or MAP4 derived peptide comprising at least one of the Serine or Threonine residues of MAP2, MAP2c or MAP4:

MAP2/MAP2c: S37, S1536, S1676, S1707, S1792, S1796, S1799

MAP4: T829, T873, T874, T876, S899, S903, S928, S941, S1073

The terms "tau derived peptide comprising the Ser262 residue and a MAP2, 2c or MAP4 derived peptide comprising at least one of the Serine or Threonine residues of MAP2, MAP2c and MAP4:

MAP2/MAP2c: S37, S1536, S1676, S1707, S1792, S1796, S1799

MAP4: T829, T873, T874, T876, S899, S903, S928, S941, S1073"

as used herein refers to a peptide which in its three dimensional structure reconstitutes the natural conformation of the tau protein or the MAP2, 2c or 4 proteins with regard to the epitope comprising Serine residue 262 (tau) or the other residues referred to above (MAP) MAP2, MAP2c and MAP4. These peptides will mimic the natural substrate (i.e. tau or tau related MAPs) of the NPK of the invention, but will not display any NPK associated biological effect. The synthesis of said peptides which solely may consist of the epitopes, or may comprise additional flanking amino acids, is well known in the art.

The present invention further relates to a diagnostic composition comprising:
(a) the NPK of the invention;
(b) the antibody or fragment or derivative of the invention; and/or
(c) apeptide comprising the phosphorylatable Serines or Threonines of tau, MAP2, MAP2c or MAP4 indicated above.

Said diagnostic composition may, for example, be used for the detection of Alzheimer's disease or cancer or the onset thereof. The antibody of the invention may be used to detect abnormal, in particular higher concentrations or levels, of the NPK of the invention, a higher degree of activation of said NPK, which are indicative of said diseases. The NPK delivered with the composition could be used as an internal control. On the other hand, the above defined peptides may be used as substrates to detect an abnormal activity of the NPK of the invention. Again, the activity of the NPK comprised in the diagnostic composition may serve as an internal control.

The antibody specifically binding to the phosphorylated Serine residues enumerated above and comprised in MAP4, MAP2 or MAP2c may be used to detect an abnormal phosphorylation status or pattern of these microtubule associated proteins which is indicative of cancer.

Further applications of the diagnostic composition are as follows. Thus, in one embodiment, said diagnostic composition may comprise an antibody of the invention directed to one of the epitopes referred to above. For example, an Alzheimer's or cancer correlated disease state of a sample may be detected by treating said sample with an antibody recognising one or more of said epitopes. The antibody-epitope (hapten) complex may be visualised using a second antibody directed to the antibody of the invention and being labelled according to methods known in the art (see, for example, Harlow and Lane, ibid.).

In still another embodiment of the present invention, said diagnostic composition may consist of an epitope referred to above and an antibody of the invention. Treatment of a sample with said antibody may give rise to conclusions with regard to the disease state of the corresponding patent, if the binding of said antibody to said sample is brought in relation to binding of said antibody to said epitope referred to above used as a reference sample.

In still another embodiment, the diagnostic composition may comprise an epitope referred to above, the NPK of the invention and an antibody of the invention. Kinase activity may be monitored with respect to phosphorylation of the sample as compared to the phosphorylation of the epitope of the invention. From the quantitated NPK activity the phosporylation state of the tau protein or the MAP2, 2c or 4 contained in said sample and therefore the disease state of the patient may be deduced. The kinase activity may, for example, be deduced by including a substrate analog in the same reaction, which is visually detectable upon enzymatic conversion. Such substrate analogs are widely used in the art. Alternatively, the amount of a phosphorylated tau protein or MAP2, 2c or 4 in the sample may be detected after treatment with the kinase of the invention by employing an antibody of the invention directed to the phosphorylated epitope and using the amount of antibody-epitope complex provided by the diagnostic composition as an internal standard, or by determining the amount of phosphate incorporated into tau protein or MAP2, 2c or 4 by the NPK, for example, by radioactive tracer methods which are well known in the art.

It should be kept in mind, however, that the person skilled in the art, being familiar with diagnostic principles, can easily combine the above mentioned compound in a different manner or supplement the composition with secondary or tertiary, labelled or unlabelled antibodies, or with enzymes and substrates. These embodiments are also covered by the present invention.

In still another embodiment, the invention relates to a method for the in vitro diagnosis and/or monitoring of Alzheimer's disease comprising assaying a cerebrospinal fluid isolate of patient or carrying out a biopsy of nerve tissue (for example, olfactory epithilium) and testing said tissue for the presence of the NPK of the invention.

The invention further relates to a method for the in vitro diagnosis and/or monitoring of Alzheimer's disease comprising assaying a cerebrospinal fluid isolate of a patient or carrying out a biopsy of nerve tissue and testing said tissue for the presence of unphysiological amounts of the NPK of the invention, or for unphysiological activity of said NPK.

An example of a nerve tissue suitable for said biopsy is the olfactory epithelium.

The method of the invention may, for example, be carried out by using the diagnostic composition of the invention, in particular the antibody directed to said NPK. Therefore, in a preferred embodiment of the invention, the NPK of the invention is detected by the antibody of the invention specifically binding to said NPK.

Additionally, the invention relates to a method for the in vitro diagnosis for cancer or the onset of cancer comprising assaying a suitable tissue or body fluid for the presence of phosphorylated Serine or Threonine residues of tau related microtubule associated proteins (MAPs) MAP2, MAP2c and MAP4 in the positions:

MAP2/MAP2c: S37, S1536, S1676, S1707, S1792, S1796, S1799

MAP4: T829, T873, T874, T876, S899, S903, S928, S941, S1073"

or for the presence of unphysiological amounts of the NPK of the invention or an NPK specific phosphatase. It is understood that the phosphorylation status of the Serine or Threonine residues has to be an unphysiological one. Methods for determining such a phosphorylation status have been described in detail in PCT/EP 92 02 829, which is incorporated herein by reference.

The assay for said phosphorylated Serine or Threonine residues may, for example, be carried out using an antibody specifically detecting said phosphorylated residues or the epitopes comprising said residues.

The amount of the NPK in the sample may be measured by using antibodies specifically directed thereto or by measuring their activity using a suitable substrate, for example, a peptide comprising the above referenced Serine or Threonine in a non-phosphorylated state or any of MAP2, MAP2c and MAP4 in unphosphorylated state. Methods for measuring the phosphorylation status of proteins have been described in detail in PCT/EP; 92 02 829. The activity of the phosphatases, for example PP-2A, PPI or calcineurin may be tested by providing the substrate, NPK of the invention, for example, comprised in the diagnostic composition of the invention.

A suitable tissue or body fluid for carrying out this in vitro method of the invention is cerebrospinal fluid, blood, biopsies of tissue (for example, liver or skin).

Still another object of the invention is to provide a method for the in vitro conversion of normal MAP2, MAP2c or MAP4 by the treatment with the NPK of the invention into proteins phosphorylated at positions:

MAP2/MAP2c: S37, S1536, S1676, S1707, S1792, S1796, S1799

MAP4: T829, T873, T874, T876, S899, S903, S928, S941, S1073"

said phosphorylation status being indicative of cancer or the onset of cancer. The conditions allowing the phosphorylation of said MAPs can be determined by following the general teachings provided by the present application. The phosphorylated MAPs can then be recognised by specific antibodies. The results of said in vitro method will allow further insights into the generation of cancer.

Moreover, inhibitors may be tested which prevent the conversion of normal to MAP protein phosphorylated in the positions indicated above. These "inhibitors" may be specific for the epitope to be phosphorylated by, for example, blocking the epitope, or may be directed to various domains on the protein kinase of the invention, NPK, as long as they prevent or disturb its biological activity. Another type of inhibition is the antagonistic action of phosphatases on said MAPs or said NPK, or the inhibition of the activating kinase of said NPK. Furthermore, the MAP generated by the method of the present invention may be employed in binding studies to microtubule structures in vitro and in vivo, thus contributing to the elucidation of the molecular basis underlying cancer.

The present invention relates, moreover, to the use of the phosphorylated Serine or Threonine residue(s) of the MAP of the invention or the epitope comprising said residue(s) for the generation of specific antibodies indicative of cancer or the onset of cancer.

The methods for obtaining said antibodies are well known in the art; thus, the generation of polyclonal or monoclonal antibodies may be conducted using standard methods (see, for example, Harlow and Lane, ibid.). If an oligo- or polypeptide is used for the generation of antibodies, it is desirable to couple the peptide comprising the epitope to a suitable carrier molecule capable of inducing or enhancing the immune response to said epitope, such as bovine serum albumin or keyhole limpet hemocyanin. The methods of coupling hapten (comprising or being identical to the epitope) and carrier are also well known in the art (Harlow and Lane, ibid.). It is also to be understood that any animal suitable to generate the desired antibodies may be used therefor.

THE FIGURES SHOW

FIG. 1: Bar diagram of tau (isoform htau40, the largest one in central nervous tissue, Goedert et al., 1989), construct K18 containing the four repeats, and several sites phosphorylated by the kinase activity from brain (Gustke et al., 1992). The hatched boxes near the N-terminus are inserts which may be absent because of differential splicing, the boxes labelled 1–4 represent the four repeats, of which repeat 2 may be absent. Most phosphorylated sites are in Ser-Pro or Thr-Pro motifs outside the repeats, but the brain kinase activity also phosphorylates two sites within the repeats, Ser262 and Ser356.

FIGS. 2A–2E: Isolation of NPK110 from porcine brain. (A) The tissue extract was loaded onto phosphocellulose and eluted stepwise with 0.15–1 M NaCl. The filled bars show the total protein concentration of the eluted material, open bars show the activity as measured with tau construct K18 as substrate. (B) The material eluted with 0.35–0.5 M NaCl was submitted to ammonium sulfate precipitation and the precipitate dialysed and loaded onto a Q-Sepharose column. The closed symbols show the protein concentration, open symbols the activity profile. The gradient composition is indicated on the right axis. (C) Fractions 8–15 from Q-Sepharose were dialysed and loaded onto a SP-Sepharose column. (D) Fractions 12–16 from SP-Sepharose were dialysed and loaded onto a Mono Q HR 5/5 column. (E) Fractions 9–11 from Mono Q were loaded onto a Superdex 200 gel filtration column. The elution positions of molecular weight markers are indicated on the right axis.

FIG. 3: Final purification of NPK110 by affinity chromatography on ATP-Sepharose (SDS PAGE, lanes 1–3) and characterisation by in-gel phosphorylation (autoradiography, lanes 4–6). The most active fractions from the gel filtration column (lane 1) were loaded onto an ATP affinity column. The kinase was eluted specifically with 5 mM ATP (lanes 2, 3). The silver stained gel shows a fuzzy band with an apparent molecular weight of approximately 110 kDal and a second, sharp band with 95 kDal. Lanes 4–6 show autoradiograms of the in-gel phosphorylation of the samples in lanes 1–3. As a substrate, tau (5 μM) was polymerised into the gel matrix. After renaturation and incubation with g-$^{32}$P ATP, it is clearly shown that only the 110 kDal band displays kinase activity towards tau.

Figure 4:
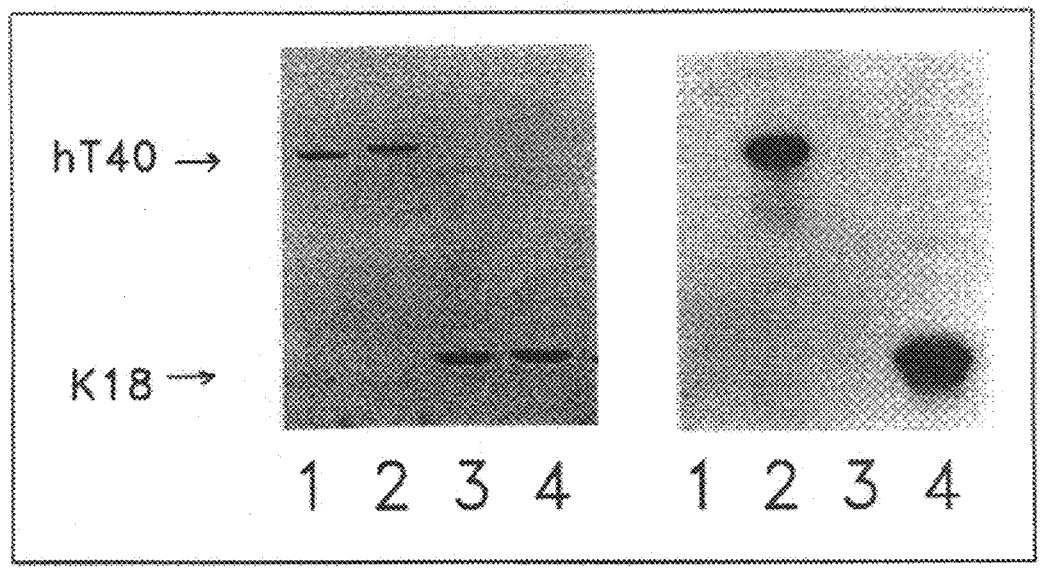

FIG. 4: Phosphorylation of wild type tau and construct K18 (microtubule binding domain) by NPK110. Htau40 (10 μM, lanes 1, 2) and K18 (20 μM, lanes 3, 4) were phosphorylated with 5 μU/ml of NPK110 and 2 mM g-$^{32}$P-ATP at 37° C. for 2 hours. Aliquots were electrophoresed on a 7–20% SDS gradient gel: Lanes 1, 2, htau40 before and after phosphorylation, lanes 3, 4, K18 before and after phosphorylation. Note the small molecular weight shift upon phosphorylation in lanes 2 and 4. The right side shows an autoradiograph of the same gel; phosphorylated htau40 and K18 are seen in lanes 2 and 4.

FIGS. 5A–5D: Tryptic phosphopeptide maps of wild type tau (htau40) and construct K18 phosphorylated with NPK110. 30 μg of tau were phosphorylated with 0.5 μU NPK110 for 2 h at 37° C. (A) full length 4-repeat tau (htau40 ), (B) construct K18 (MT binding region, residues 244–372 of full length tau), (C) diagram of the more prominent spots: Spot 1 on upper left contains Ser262, spot 2 on upper right Ser356, spot 3 (below 1) Ser305, spot 4 (always part of an overlapping doublet) contained Ser324, spot 5 Ser293 (this tryptic peptide CGSK was not recovered from the HPLC column, presumably because of its small size, but the spot could be identified by site-directed mutagenesis) (D) Mixture of identical amounts of counts (10,000 cpm) derived from phosphopeptides shown in (A) and (B). The identification of phosphorylation sites shown in (C) was performed by two dimensional analysis of the HPLC-purified and sequenced peptides (listed in Table 1). 10,000 cpm of the purified peptides each were analysed alone and in combination with a 5000 cpm aliquot of the phosphopeptides shown in (A) in order to allow unambiguous identification.

FIGS. 6A–6B: Phosphorylation of Ser262 abolishes the binding of tau to microtubules. (A) Binding of tau to taxol-stabilised microtubules (30 μM) was measured in a cosedimentation assay as described below in Example 2. Full length wild-type tau ('wt', htau40 ) and a Ser262 to Ala mutant (A262) (10 μM) were previously phosphorylated with NPK110 (final concentration 8.5 μU/ml) for 2 hours at 37° C. Curves were obtained by non-linear regression (Biernat et al., 1993). The binding of wild-type tau is completely abolished by phosphorylation (closed circles), whereas the A262 mutant still binds, although with lower affinity (triangles). For comparison, the binding of unphosphorylated tau is also shown (open circles).

(B) Microtubule-bound tau comes off during phosphorylation by NPK110. htau 40 (10 μM) was incubated with taxol-stabilised microtubules (30 μM). At t=0, NPK110 was added to a final concentration of 10 μU/ml, and aliquots were withdrawn at time intervals from one to 20 hours and pelleted. Tau was measured in the pellets and supernatants by densitometry of the SDS gels (closed circles). Incorporated phosphate was measured by Cerenkov counting of gel pieces (open circles) and is indicated on the right axis. Phosphate incorporation in tau without microtubules is shown to proceed faster (squares).

FIGS. 7A–7B: Dark field video microscopy of microtubules and effect of phosphorylation of Ser262 on tau. Microtubules (5 μM tubulin) were nucleated on sea urchin sperm axonemes in the presence of 2.5 μM tau (isoform htau40) and 10 μU/ml of NPK110. A, 20 min without ATP, B, with ATP. In A the microtubules grow continuously, in B Ser262 can be phosphorylated, leading to a destabilisation and shortening of microtubules. Bar=10 μm.

FIGS. 8A–8E: Effect of the unphosphorylated and NPK110-phosphorylated tau on the length of axoneme nucleated microtubules measured by darkfield microscopy. For each condition 500 to 600 microtubule plus ends were measured; the mean length was plotted against time. Tubulin concentration was 5 μM; note that without added tau, no microtubules are observed at this concentration. Tau was 2.5 μM in all cases. In control experiments, ATP was omitted ('-ATP').

(A) Tau pre-phosphorylated by NPK110 does not promote microtubule growth (filled circles) but the pre-phosphorylated point mutant A262 does (triangles, in accordance with time resolved binding assay in FIG. 6B).

(B) Tubulin and tau were mixed at 4° C. with 10 μU/ml of NPK110 (final concentration) in the presence (closed circles) or absence (open, circles) of 2 mM Mg-ATP. At t=0, the temperature was raised to 37° C. With wild type tau and no ATP, microtubules grow continuously (open circles); the same result is obtained with the mutant Ser262-Ala (triangles). However, wild type tau plus ATP leads to initial growth but subsequent shrinkage (closed circles).

(C–E) Microtubule length histograms at 5 min and 30 min of the corresponding, curves in B. Each sample shows a pronounced peak around 20cm after 5 min (empty circles) If Mg-ATP was absent (C) or Ser262 was mutated into Ala (E) the distribution became broader and shifted to greater lengths at 30 min. By contrast, phosphorylation of tau successfully decreased the mean microtubule length within 30 min of incubation (D).

FIGS. 9A–9D: Tryptic phosphopeptide maps of wild type tau (htau40 ) and construct K18 phosphorylated with (A) brain extract, (B) NPK110, (C) PKC, or (D) PKA, respectively. The numbering of the spots is analogous to FIG. 5 (spot 1:Ser262, spot 2:Ser356, spot 3:Ser305, spot 4:Ser324, spot 5:Ser293). The panels on the right show the corresponding two-dimensional phosphoamino acid analysis of full length tau for each kinase.

Figure 10:
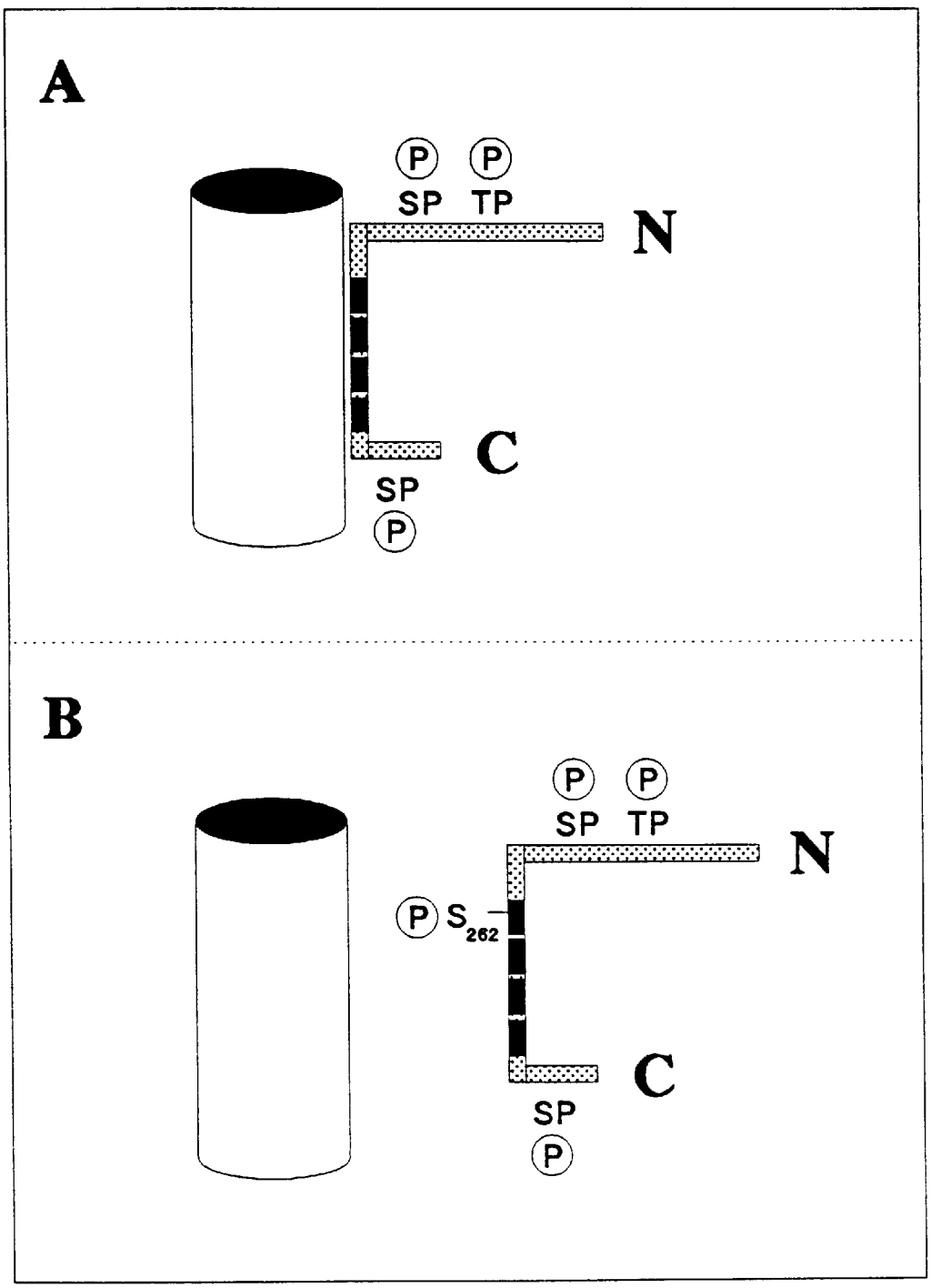

FIGS. 10A–10B: Diagram representing the influence of different phosphorylation sites on tau-microtubule interactions. The majority of Ser/Thr-Pro motifs are in the flanking regions of the repeat domain, they have only a small influence on the binding of tau. The repeat domain contains several phosphorylatable non-Ser-Pro sites, especially the four KXGS motifs. Of these, Ser262 in the first KIGS motif has by far the greatest influence on microtubule binding.

Figure 11:
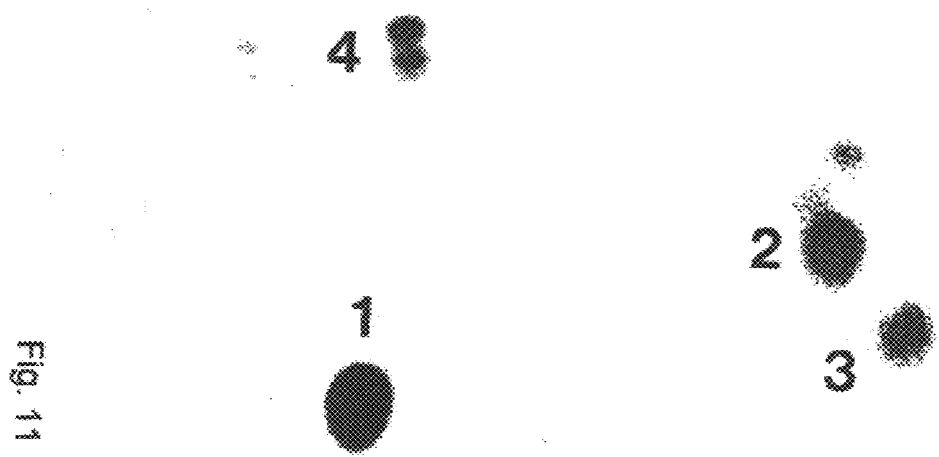

FIG. 11: Phosphopeptide map of, recombinant MAP2c phosphorylated by NPK-110. The peptides contain the following phosphorylated residues: I=Ser1707, II=Ser1676, III=Ser37 and Ser1536, IV=Ser1792, Ser1796 and Ser1799 (numbering of residues following Albala et al., 1993).

Figure 12:
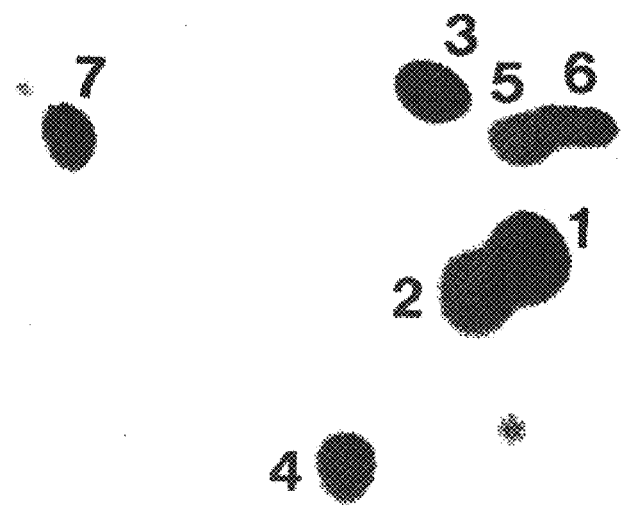

FIG. 12: Phosphopeptide map of MAP4 fusion protein phosphorylated by NPK-110. The peptides contain the following phosphorylated residues: I=Thr829, II=Ser941, III=Ser928, IV=Thr873, Thr874 and Thr876, V=Ser899 and Ser903, VI=Ser1073, VII=Ser928 (numbering of residues following West et al., 1991).

FIGS. 13A–13C: Effect of the unphosphorylated and NPK-110-phosphorylated MAP4, MAP2 and MAP2c on the length of axoneme nucleated microtubules measured by darkfield microscopy. For each condition 500 to 600 microtubule plus ends were measured; the mean length was plotted against time. Tubulin concentration was 5 μM; MAPs were 1 μM. Note that without added MAPs, no microtubules were observed at this concentration.

(a) Tubulin and MAP4 were mixed at 4° C. with 10 μU/ml of NPK-110 (final concentration in the presence (closed circles) or absence (open circles) of 2 mM Mg-ATP. At t=0, the temperature was raised to 37° C. With MAP4 and no ATP, microtubules grow continuously (open circles). However, MAP4 plus ATP leads to initial growth but subsequent shrinkage (closed circles) because MAP4 becomes phosphorylated, detaches from microtubules, and microtubules are destabilised.

(b) Same experiment as in (a) but using MAP2, with similar results.

(c) Same experiment as in (a) but using MAP2c, with similar results.

Figure 14:
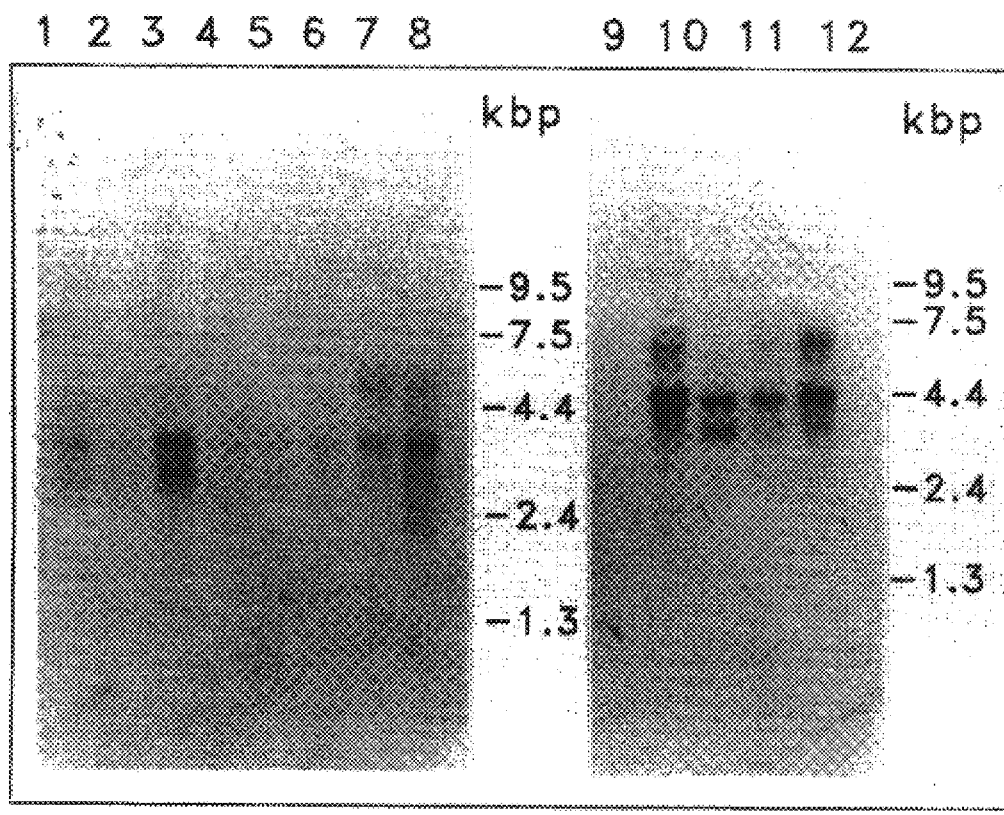

FIG. 14: Northern Blot of adult and fetal human tissues with a MARK cDNA probe.

left: adult tissue
lane 1: Pancreas (Pa)
lane 2: Kidney (Ki)
lane 3: Muscle (Mu)
lane 4: Liver (Li)
lane 5: Lung (Lu)
lane 6: Placenta (Pl)
lane 7: Brain (Br)
lane 8: Heart (H);

Right: fetal tissue
lane 9: Kidney (Ki)
lane 10: Liver (Li)
lane 11: Lung (Lu)
lane 12: Brain (Br)

Figure 15:
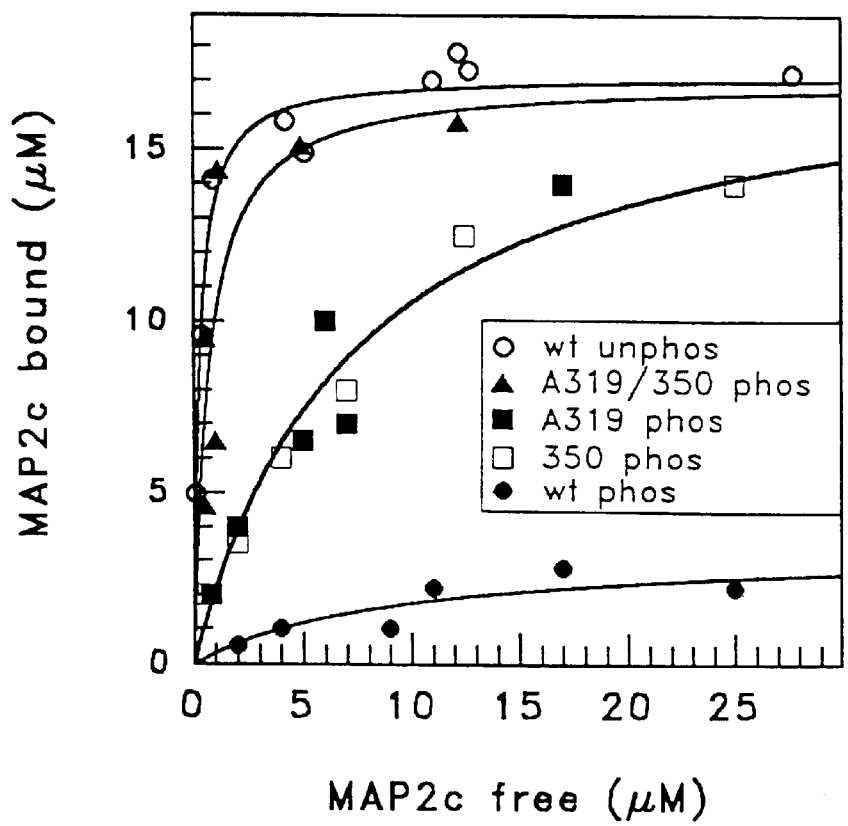
Figure 16:
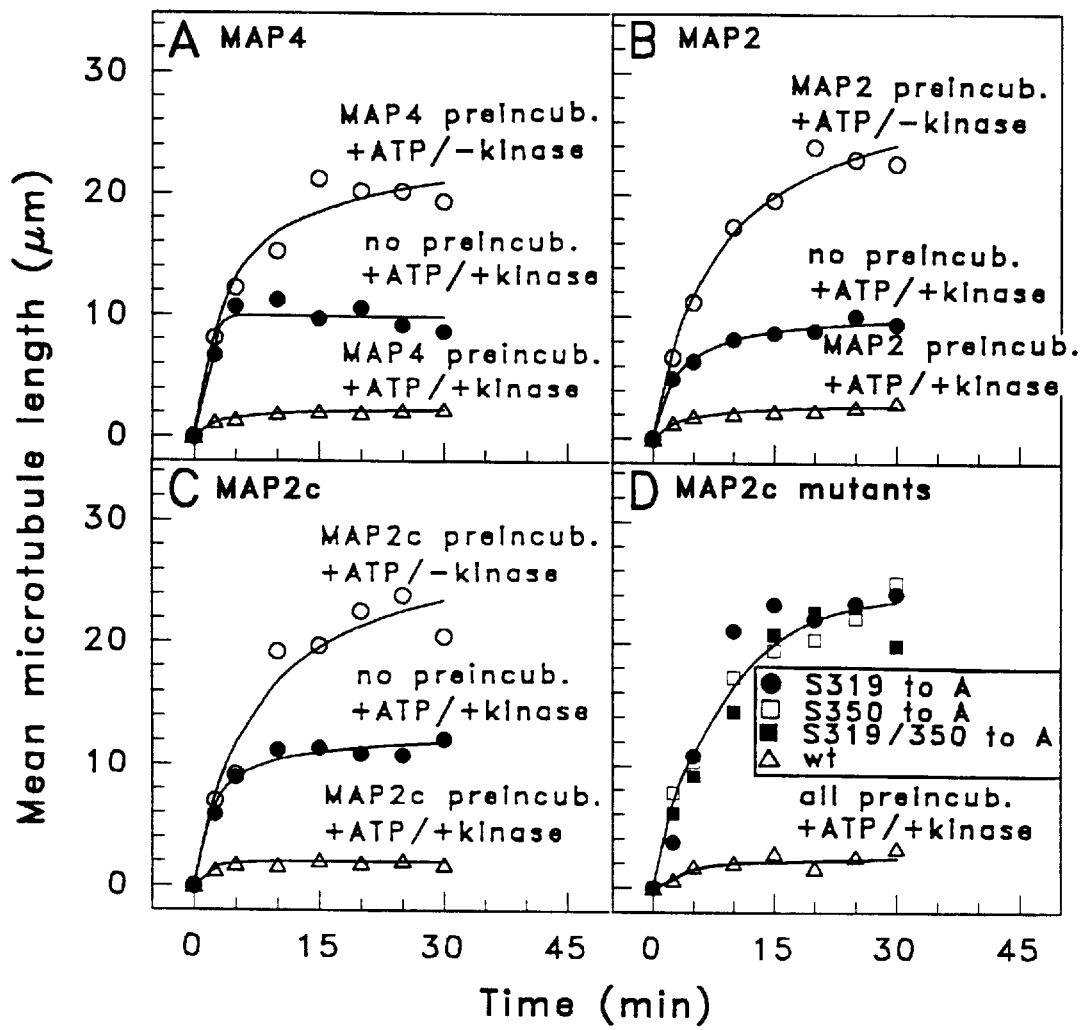

FIG. 15: Binding of recombinant wild type MAP2c and MAP2c point mutants to taxol stabilized microtubules (30 μM tubulin dimers) under the influence of phosphorylation by p110MARK. Open circles: wild-type MAP2c, non-phosphorylated. The binding is tight (Kd about 0.25 μM) and saturates around 17 μM ligand, or about 1 MAP2c molecule per 2 tubulin dimers. Closed circles: wild-type MAP2c, phosphorylated previously with p110MARK (2.5 milliUnits/ml; 1 Unit corresponds to 1 μmol of phosphate transferred to MAP2c per minute at 30° C.) for 2 h. Note that there is essentially no binding. Closed and open squares: MAP2cA319 and MAP2cA350, phosphorylated previously with p110MARK (2.5 milliUnits/ml) for 2 h. In these mutants the serines 319 or 350 in the KXGS motifs in the first or second repeat were point mutated to alanines. The affinity to microtubules decreases markedly (Kd≈7 μM) although the stoichiometry remains similar to the wildtype MAP2c. Triangles: MAP2cA319/A350, phosphorylated previously with p110mark (2.5 milliUnits/ml) for 2 h. In this mutant both serines 319 and 350 are mutated to alanines. The binding is similar to the unphosphorylated protein, showing that the sensitivity to phosphorylation has disappeared because the two KXGS motifs are no longer phosphorylatable.

FIGS. 16A–16D: Effects of unphosphorylated and p110MARK-phosphorylated MAP4 (A), MAP2 (B), MAP2c (C) and MAP2c point mutants (D) on the length of self-nucleated microtubules measured by darkfield microscopy. For each condition 500–800 microtubules were analyzed, and the mean length were plotted against time. Tubulin concentration was 10 μM in all cases, the concentration of MAP4 and MAP2 was 1 μM, that of MAP2c 2 μM. In control experiments, ATP was omitted ('-ATP').

Open circles in A, B and C: The MAPs were preincubated for 30 min with 2.5 mUnits/ml p110MARK (final concentration), but without ATP. By adding 10 μM tubulin, microtubules were nucleated and the mean microtubule length increased up to about 20 μm within 30 min. By contrast, if ATP was present no self-nucleation occurred, showing that the phosphorylation of the MAPs prevented microtubule formation. Short microtubules of about 2 um length could only be observed by adding axonemes (10–100 fM) to promote seeded nucleation (open triangles in A, B, C).

Closed circles in A, B, and C: Tubulin and MAP were mixed at 4° C. with 2.5 mUnits/ml of p110MARK (final concentration), and the temperature was shifted immediately to 37° C. (so that initially the MAPs were unphosphorylated). Microtubule growth was promoted in all three cases, but the final mean microtubule length was only about half of that observed for the unphosphorylated MAPs (compare open circles).

D: The effect of phosphorylation site point mutations of MAP2c. All proteins were phosporylated as described above (with 30 min preincubation). Triangles; wildtype MAP2c, closed circles; MAP2cA319 (KXGS in first repeat mutated to KXGA), squares; MAP2cA350 (KXGS in second repeat mutated to KXGA), closed squares; MAP2cA319/A350 (KXGS in both repeats mutated to KXGA).

THE EXAMPLES ILLUSTRATE THE INVENTION

Regarding the tau proteins described in the examples, only recombinant human tau proteins expressed in *E. coli* were used. cDNA clones were prepared as described by M. Goedert (Goedert et al., 1989) and were expressed using variants of the pET expression vector (Studier et al., 1990). The proteins were purified making use of the heat stability of tau and Mono S FPLC (Hagestedt et al., 1989). Construct K18 is derived from the 4-repeat tau isoform and comprises the microtubule binding region, residues 244 to 372 (Biernat et al., 1993). Mutant 'A262' is based on the longest human isoform. A single residue, Ser262, was changed into alanine using conventional technology. Phosphocellulose-purified tubulin (PC-tubulin) was prepared from porcine brain following Mandelkow et al., 1985. Protein kinase A catalytic subunit (isolated from bovine heart, activity 27 catalytic subunit (isolated from bovine heart, activity 27 nU/Al based on kemptide, 100 pU/μl based on casein) was obtained from Promega, Protein kinase C (isolated from rat brain, activity 80 pU/μl based on histone H1) was from Boehringer Mannheim.

EXAMPLE 1

Purification and Characterisation of the Protein Kinase NPK110

All operations were performed at 4° C. Fresh porcine brains (approx. 1 kg) were obtained at the local slaughterhouse and homogenised into 1 liter of buffer A (50 mM Tris, pH 8.5, containing 5 mM EGTA, 100 mM NaF, 1 mM PMSF, 1 mM benzamidine, 1 mM Na$_3$VO$_4$, 1 mM DTT, 0.1% Brij-35). The homogenate was transported to the laboratory on ice and centrifuged at 30,000 g for 1 h. The supernatant was cleared by ultracentrifugation (50,000 g, 30 min), the pH adjusted to 6.8 and loaded onto a Buchner funnel containing 150 ml Whatman P11 equilibrated with buffer B (50 mM MES pH 6.8, 2 mM EGTA, 50 mM NaF, 1 mM PMSF, 1 mM benzamidine, 1 mM Na$_3$VO$_4$, 1 mM DTT, 0.1% Brij-35), by applying a slight vacuum. The phosphocellulose was washed with 500 ml of buffer B and eluted stepwise with 150 ml each of buffer B containing 0.15 M–1 M NaCl (FIG. 2A). Fractions were screened for activity by phosphorylation of a tau construct (K18) consisting of the four microtubule binding repeats, essentially as described (Drewes et al., 1992). Active fractions were fractionated by ammonium sulfate precipitation. The precipitate obtained between 30 and 50% saturation was dialysed against buffer A overnight on ice. The dialysate (approx. 50 ml) was cleared by ultracentrifugation and loaded onto an anion exchange column (Q-Sepharose HR, Pharmacia, 80×16 mm) using a Superloop (Pharmacia). After washing the column with 100 ml of buffer A and elution with a stepwise gradient from 0–0.5 M NaCl (FIG. 2B, flow rate 5 ml/min, fraction size 7 ml), active fractions (approx. 40 ml) were dialysed against buffer B and loaded onto a cation exchange column (SP-Sepharose HR, Pharmacia, 60×16 mm) (FIG. 2C, flow rate 4 ml/min, fraction size 7 ml). After elution with 0–0.5 M NaCl, active fractions (approx 40 ml) were pooled, the buffer was changed for buffer A on a Sephadex G25 column (300×26mm) and loaded onto a Mono Q HR 5/5 column (Pharmacia) and eluted with a steep NaCl gradient (FIG. 2D, flow rate 0.5 ml/min, fraction size 1 ml). Active fractions (2–3 ml) were concentrated twofold in a Centricon 30 microconcentrator (Amicon) and loaded onto a gel filtration column (Superdex 200, Pharmacia, 300×16 mm) equilibrated and eluted with buffer A (pH 7.8, containing 150 mM NaCl and 10% glycerol). The flow rate was 0.2 ml/min, fraction size was 2 ml. The column had previously been calibrated with a marker protein kit (Pharmacia). Active fractions were pooled, and the buffer was changed to buffer C (40 mM β-glycerophosphate, 10 mM MgCl$_2$, 2 mM EGTA, 1 mM Benzamidine, 0.2 mM DTT, 0.1% Brij-35) on a Sephadex G25 column ( 100× 16mm). The protein pool from the G25 column (10–15 ml) was loaded at 0.1 ml/min onto an ATP-Sepharose column (Upstate Biotechnology Inc., Lake Placid, USA, 15×5 mm). The column was washed with 5 ml of buffer C and eluted with 2 ml of buffer C containing 5 mM MgATP. The eluate was concentrated and freed from ATP and buffer substances on a Mono Q PC 1.6/5 column ('Smart' system, Pharmacia), eluted with 25 mM Tris-HCl , pH 7.4, containing 250 mM NaCl, 1 mM EGTA, 0.2mM DTT, 1 mM benzamidine and 0.03% Brij-35. Active fractions were mixed with 50% (v/v) glycerol and stored at −20° C. Under these conditions, activity was preserved for at least one month.

With these six chromatographic steps used a ≈10,000 fold purification of a Ser262-phosphorylating activity from a porcine brain tissue extract was achieved. As shown in detail in FIG. 2, phosphocellulose (A), ion exchange chromatography on Q- and SP-Sepharose and Mono Q (B,C,D), gel filtration (E) and, finally, affinity chromatography using immobilised ATP were employed. The activity of this kinase in the tissue extract was ≈0.2 mU/mg, the activity of the affinity-purified kinase ≈2 U/mg (1 unit transfers 1 Amol of phosphate per minute). The molecular weight of the enzyme was around 90–100 kDal by gel filtration, but the activity peak was broad and often showed pronounced tailing (FIG. 2E). On SDS gels, the apparent molecular weight was ≈110 kDal (FIG. 3). The enzyme could be renatured in the gel; if tau was polymerised into the gel matrix as a substrate and the gel was incubated with γ-$^{32}$P-ATP, the 110 kDal band became prominent upon autoradiography (FIG. 3, lane 4–6), whereas some minor contaminations observed in the silver stained gel had no detectable activity. After phosphorylation with NPK-110, both whole tau and construct K18 showed small but distinct mobility change in SDS PAGE (FIG. 4, lanes 1–4). The final amount of incorporated phosphate is ≈1.8–2.5 mol per mole of tau, depending somewhat on enzyme concentration and activity; this level of phosphorylation could be achieved after ≈2 hours. Phosphorylation reactions were carried out as follows:

Phosphorylation reactions were carried out in 40 mM Hepes, pH 7.2, containing 2 mM ATP, 5 mM MgCl$_2$, 2 mM EGTA; 1 mM DTT, 0.1 mM PMSF, 0.03% Brij-35. When extracts or crude fractions of kinase preparations were screened, 50 mM NaF or 1 μM okadaic acid (LC Services, Woburn, Mass., USA) was included. Reactions were terminated by heating to 95° C. Phosphorylation was assayed in SDS gels (Steiner et al., 1990) or on phosphocellulose paper discs (Gibco) (Casnellie, 1991). In-gel phosphorylation assays were performed according to the method of Geahlen et al., 1986.

Figure 5:
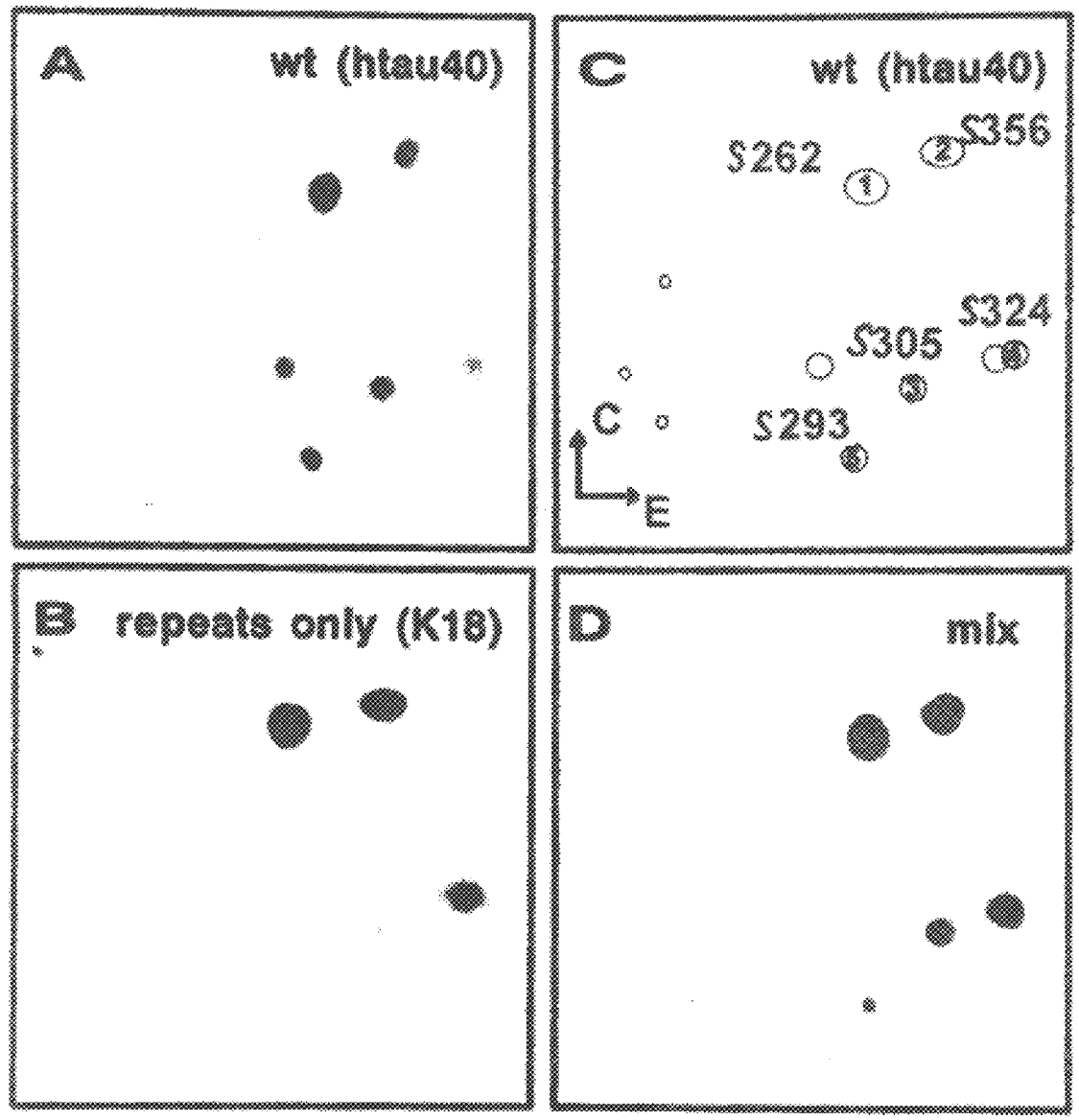

The specificity of NPK110 for tau was examined by tryptic digestion of phosphorylated protein and subsequent two-dimensional thin layer electrophoresis and chromatography (FIG. 5). If one compares the phosphorylation patterns obtained from recombinant full-length 4-repeat tau (FIG. 5A) and the 4-repeat fragment K18 (FIG. 5B), it is apparent that most phosphorylated peptides are generated from the repeat domain. This was confirmed by analysis of a mixture of both samples (FIG. 5D). In a second approach, the tryptic digest was resolved by HPLC (not shown). In more detail, these approaches were carried out as follows:

Following phosphorylation reactions, the kinases were removed by boiling of the samples in 0.5 M NaCl/10 mM DTT and centrifugation. Tau protein remains in the supernatant and was precipitated by 15% TCA. Cysteine residues were modified by performic acid treatment (Hirs, 1967). The protein was digested overnight with trypsin (Promega, sequencing grade) in the presence of 0.1 mM CaCl$_2$, using two additions of the enzyme in a ratio of 1:10–1:20 (w/w). Two-dimensional phosphopeptide mapping on thin layer cellulose plates (Macherey & Nagel, Duren, FRG) was performed according to Boyle et al., 1991. In brief, first dimension electrophoresis was carried out at pH 1.9 in formic acid (88%)/acetic acid/water (50/156/1794), second dimension chromatography in n-butanol/pyridine/acetic acid/water (150/100/30/120). For the mapping of phosphorylation sites by sequencing, recombinant human tau (200 μg, clone htau 40) was phosphorylated with NPK110 and $^{32}$P-ATP (100 Ci/mol) for 2 hours. The phosphorylation was terminated by a brief heat treatment. The protein was incubated with 6 M urea and 2 mM DTT, and cysteines were blocked with vinylpyridine (Tarr et al., 1983) or performic acid treatment. After dialysis against 10 mM ammonium bicarbonate, the protein was lyophilised and digested with trypsin (1:20) in the presence of 0.1 mM CaCl$_2$. Separation of peptides was performed by two successive HPLC runs on a μRPC C2/C18 SC 2.1/10 column ('Smart' system, Pharmacia). The digest was acidified with acetic acid (5% v/v) and fractionated by HPLC using a gradient of acetonitrile in 10 mM ammoniumacetate (flow rate 0.1 ml/min, 0–25% in 120 min, 25–50% in 20 min). Peptides were detected by UV absorption at 214, 254 and 280 nm and incorporated phosphate was measured as Cerenkov radiation in a scintillation counter (Hewlett-Packard TriCarb 1900 CA). Flowthrough fractions and radioactive peaks from this gradient were further purified using a gradient of acetonitrile in TFA (flow rate 0.1 ml/min, 0% acetonitrile/0.075% TFA to 66% acetonitrile/0.05% TFA in 60 min). Sequence analysis of peptides was performed using a 477A pulsed liquid phase sequencer and a 120A online PTH amino acid analyser (Applied Biosystems). Phosphoserines were identified as the dithiothreitol adduct of dehydroalanine by gas phase sequencing (Meyer et al., 1991).

This yielded several labelled peptides which were analysed by direct phosphopeptide sequencing and by phosphoamino acid analysis. Phosphoamino acid analysis: Aliquots of digestion samples were partially hydrolysed in 6N HCl (110° C., 60 min) and analysed by two dimensional electrophoresis at pH 1.9 and pH 3.5 (Boyle et al., 1991). The results of the phosphopeptide sequencing are compiled in Table 1.

TABLE 1

Tryptic phosphopeptides from htau40 phosphorylated with NPK110, obtained by HPLC. The sequences are those of the main radioactive peaks. Listed are the number of counts obtained after the second purification run, the amount of material, the sequence with the phosphorylated residue (identified as S-ethylcysteine) starred, the phosphorylation site (numbering according to htau40). Note that the tryptic phosphopeptide CGSK from the second repeat was not detected by HPLC (presumably because of its small size and hydrophilicity) and thus had to be identified by phosphopeptide mapping and site-directed mutagenesis.

| cpm in peptide | pmoles found | Sequence found | Phosp. sites |
|---|---|---|---|
| 400.00 | 1000 | IGS*TENLK (SEQ ID NO:4) | Ser-262 |
| 150.000 | 350 | IGS*LDNIPHVPG GGNHK (SEQ ID NO:5) | Ser-356 |
| 150.000 | 300 | CGS*LGNIHHK (SEQ ID NO:6) | Ser-324 |
| 60,000 | 200 | HVPGGGS*VOLVYK (SEQ ID NO:7) | Ser-305 |

Most of the radioactivity was found in a peptide containing phosphorylated Ser262. Ser356 (in the KIGS motif of the fourth repeat) and Ser324 (from the KCGS motif of the third repeat) were also found radioactively labelled. Two dimensional analysis of these purified peptides lead to the identification of spots shown in FIG. 5C. This clearly shows that Ser262 (spot 1) is the main target site of NPK110 on tau, followed by Ser356 (spot 2). Spot 3 was identified as the peptide containing Ser305, spot 4 as Ser324 (in the KCGS motif of the third repeat), spot 5 as Ser293 (in the KCGS motif of the second repeat). The corresponding tryptic peptide ($^{291}$CGSK) could not be isolated directly by reverse phase HPLC chromatography, presumably because of its shortness and hydrophilicity. It was therefore identified by site directed mutagenesis, using point mutants of K18 where the serines in all four KXGS motifs (Ser262, 293, 324, 356) were converted into alanines. After phosphorylation with NPK110 only spot 3 (Ser305) was visible, while spots 1, 2, 4 and 5 were gone, thus identifying spot 5 with Ser293 (data not shown).

EXAMPLE 2

Tau-microtubule Binding and Dynamic Instability

Previously it was shown that the phosphorylation of Ser262 strongly decreased the interaction between tau and microtubules; that is, not only the dissociation constant increased but also the stoichiometry decreased. Confirming these observations, a similar result was obtained after phosphorylation of tau by NPK110. In fact, FIG. 6A shows that the reduction in binding is even more pronounced: NPK110 completely abolishes microtubule binding within the concentration range accessible. Because the binding became so weak it was also no longer possible to estimate values for the dissociation constant and the stoichiometry. In other words, NPK110 efficiently causes the loss of binding of tau to microtubules. Binding studies were carried out as follows:

Binding studies were performed by measuring co-sedimentation of taxol-stabilised microtubules (30 μM) and tau by ultracentrifugation (Beckman TL 100) of 30 μl-samples., Aliquots of the pellet and supernatant were assayed using SDS-PAGE and Coomassie blue staining. Scanner densitometry of dried gels was used for quantification of protein (for details see Gustke et al., 1992).

In order to verify this result, a point mutation (Ser262 to Ala) was introduced into tau so that this site could no longer be phosphorylated. In this case, incubation of the mutant with NPK110 left the microtubule binding capacity largely intact, although there was some decrease in affinity and stoichiometry (≈25%, FIG. 6A). This confirms two points of prior art studies, (i) phosphorylation of Ser262 is the major switch controlling tau's affinity for microtubules, (ii) the other sites phosphorylated by the kinase have a small but measurable effect on the binding (i.e. mainly the equivalent serines in the KXGS motifs of repeats 2, 3, and 4).

The next question was: Do microtubules protect tau from being phosphorylated by NPK110? If this were the case, then tau—once bound to microtubules—might retain its high affinity for microtubules. To answer this point, taxol-stabilised microtubules were first saturated with tau, and then incubated with NPK110. As illustrated in FIG. 6B, tau gradually dissociates from microtubules, concomitant with phosphorylation. Thus microtubules retard phosphorylation of tau by the kinase but cannot prevent it.

One important function of tau is to stabilise microtubules and suppress their dynamic instability (Drechsel et al., 1992). Thus, if tau loses its binding to microtubules one would expect stable microtubules to become dynamic. This effect can be illustrated by video dark field microscopy of individual microtubules seeded onto flagellar axonemes (FIG. 7). The experiment was carried out as follows:

Video microscopy of microtubules nucleated on axonemes was done essentially as described (Trinczek et al., 1993). Briefly, 5 μM PC-tubulin, 2.5 μM tau (unphosphorylated or phosphorylated) and low amounts of sea urchin sperm axonemes (10–100 fM) were mixed in 50 m M Na-Pipes, pH 6.9, containing 3 mM $MgCl_2$, 2 mM EGTA, 1 mM GTP and 1 mM DTT. 1.0 μl of the samples was put on a slide, covered with 18×18 mm coverslips, sealed, and warmed up to 37° C. in a temperature-controlled air flow within 5 s. A constant temperature of 37° C. was maintained by the air flow. The axoneme nucleated microtubules were recorded at time 2.5, 5, 10, 15, 20, 25, and 30 min after the temperature shift. For each condition and time three to five axonemes of a sample and 10–20 experiments were analysed, and the lengths of 500–600 microtubule plus ends were measured. Only those microtubules which were clearly located within the focal plane were taken into account. The depth of solution was 3–4 μm, and the focal depth was 1–2 μm.

Figure 8:
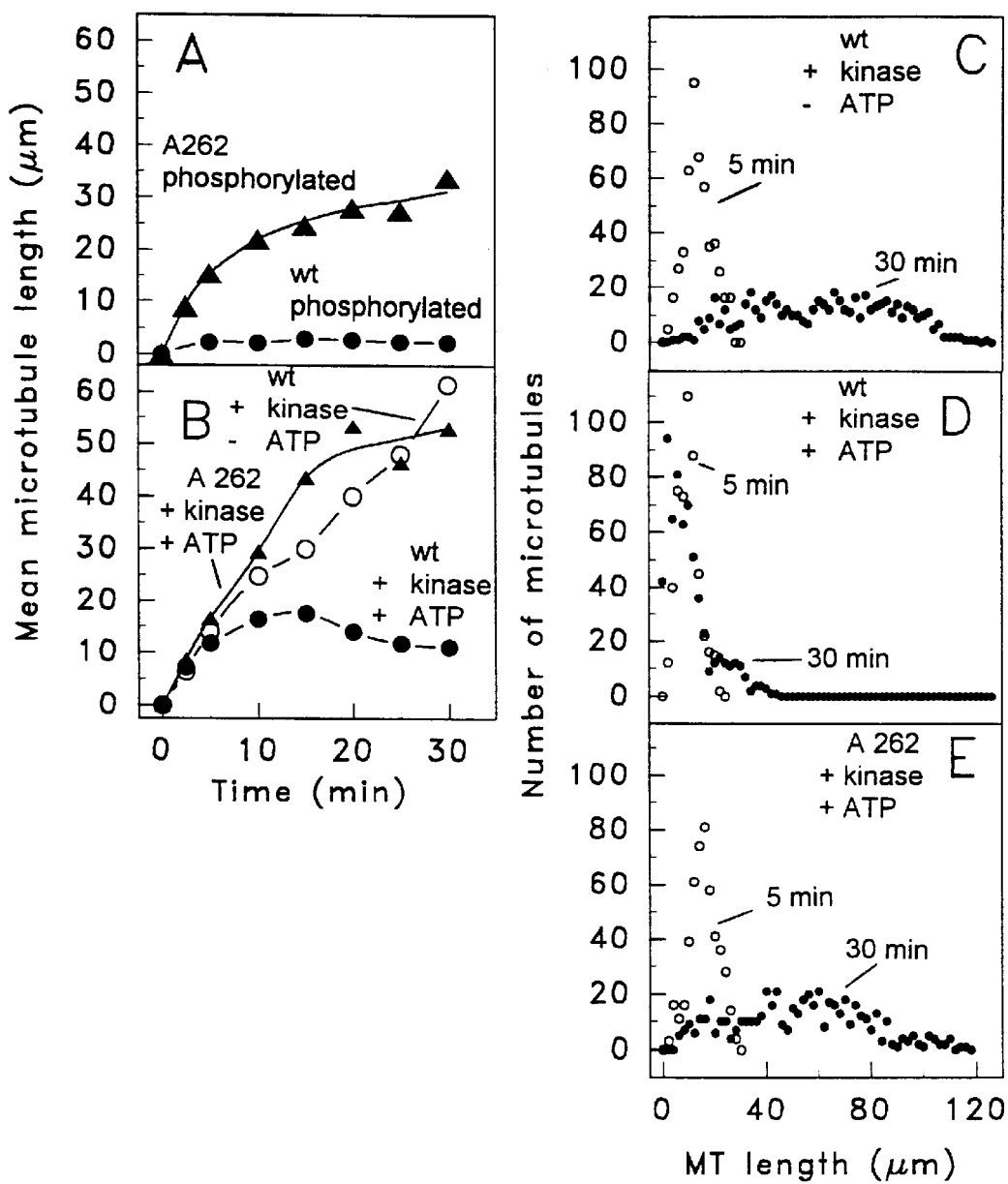

In the experiment of FIG. 8A the concentration of tubulin (5 μM) was chosen such that microtubules would not assemble by themselves but would grow upon addition of (unphosphorylated) tau. Tau phosphorylated with NPK110 did not support growth whereas the mutant Ser262-Ala did. In other words, tau, phosphorylated at Ser262 behaved as "no tau" because it did not interact with microtubules, in contrast to the mutant which did. Even more dramatic is the conversion of microtubules from undynamic to dynamic behaviour under the influence of the kinase. In the experiment of FIG. 8B microtubules were allowed to grow off axonemes in the presence of tau and their mean length which increased to ≈50 μm over 20 min was recorded. In a parallel experiment NPK110 with ATP was added (or without ATP as a control). In the control experiment (without ATP) microtubules were able to grow continuously and showed little dynamic instability (FIG. 8B, open circles). With ATP added, the mean length increased only to 20 μm and then dropped again, due to the gradual phosphorylation of tau and concomitant increase in microtubule dynamics (filled circles). When the mutant Ser262-Ala was used, microtubules grew normally even when the kinase and ATP were present (triangles). These results are summarised in the length histograms of FIGS. 8C–D. At early times after initiation of assembly microtubules are short and rather homogeneous in length (peaks of open circles at 5 min), at later times of uninterrupted growth the microtubules become long and show a broad length distribution (filled circles in FIGS. 8C and 8E). However, when the kinase is allowed to phosphorylate Ser262 (i.e. the kinase, ATP, and wild type tau with Ser262 are present), microtubules remain short (open circles in FIG. 8D).

EXAMPLE 3

Other Kinases Phosphorylating the Repeat Domain of Tau

Tau can be phosphorylated in vitro by many kinases which can be classified by several criteria, depending on function, targets, or others. Certain proline-directed kinases that are of diagnostic interest for Alzheimer's disease (because of the antibody reactions induced by them) phosphorylate the regions flanking the repeats but appear to have little influence on tau-microtubule binding. Conversely, one would expect that kinases phosphorylating the repeat region have an influence on microtubule binding because the repeats of tau are thought to be involved in this function, and this is in fact borne out by the results with NPK110 described so far. The question therefore arises how this kinase compares with other kinases phosphorylating tau in the repeat domain. Several of these have been reported so far (Table 2).

TABLE 2

Summary of phosphorylation sites and kinases affecting the repeats and nearby regions of tau (only non-proline directed kinases and sites are listed). Major sites are denoted by X, minor ones by (x). Note that the results were obtained by different methods: (1) phosphorylation of tau followed by proteolytic digestion, separation of peptides, and phosphopeptide sequencing (Steiner et al., 1990, Steiner, 1993, Gustke et al., 1992; Scott et al., 1993). (2) Mass spectrometry of phosphopeptides combined with sequencing (Hasegawa et al., 1992; Watanabe et al., 1993). (3) Phosphorylation of a synthetic peptide (Correas et al., 1992). (4) 2D mapping of phosphopeptides combined with sequencing (this report). Since these data are derived from the repeat domain K18 they do not contain information on possible phosphorylation sites outside the repeats.

| kinase or reference activity | S214 | S262 KIGS | S293 KCGS | S305 | S324 KCGS | S356 KIGS | S377 | S409 | S416 |
|---|---|---|---|---|---|---|---|---|---|
| PKA Scott et al., 1993 | (x) | | | | (x) | (x) | | x | x |
| PKA Steiner, 1993 | X | | (x) | | (x) | (x) | | X | X |
| PKA this report | ND | (x) | (x) | (x) | X | X | | ND | ND |
| PKC Correas et al., 1992 | | | | | X | | | | |
| PKC Steiner, 1993 | X | (x) | | (x) | (x) | | | X | |
| PKC this report | ND | | (x) | (x) | (x) | | | ND | |
| CaMK Steiner et al., 1990 | | | | | | | | | X |
| brain ex. Gustke et al., 1992 | | X | | | | X | | | |
| brain ex. this report | | X | | | | X | | | |
| PK 35/41 Biernat et al., 1993 | | X | (x) | | (x) | X | | | |
| NPK 110 this report | | X | (x) | (x) | (x) | X | | | |
| brain in vivo: | | | | | | | | | |
| Alzheimer: Hasegawa et al., 1992 | | X | | | | | | | |
| adult: Watanabe et al., 1993 | | no sites in repeat region | | | | | | | |
| fetal: Watanabe et al., 1993 | | no sites in repeat region | | | | | | | |

Figure 9:
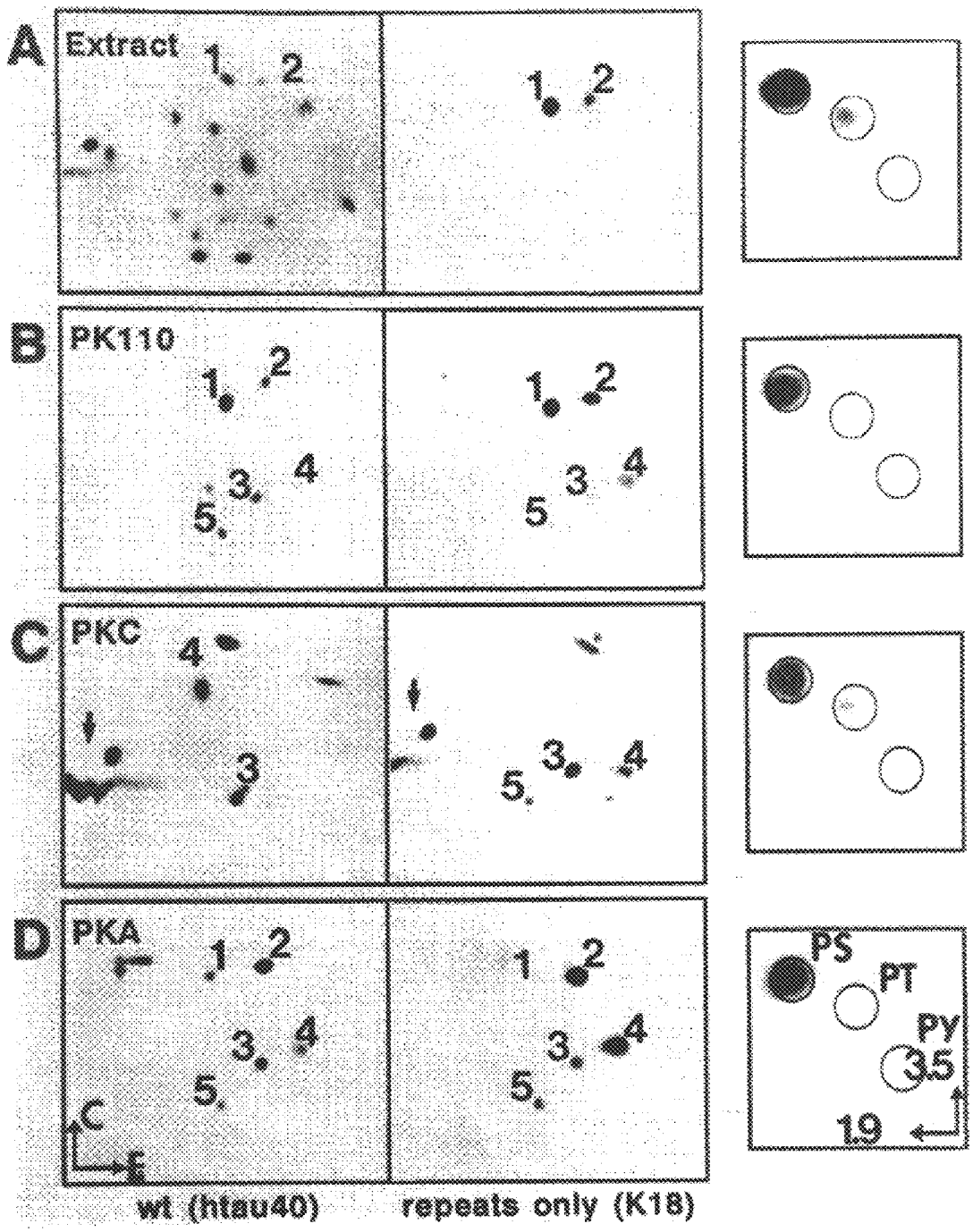

For example, PKA phosphorylates mainly Ser214, Ser409 and Ser416 outside the repeats, but minor sites include Ser324 and Ser356 within the repeats (Scott et al., 1993; Steiner, B1993). Since Ser262 is not one of the sites one would not expect a major effect on microtule binding, in agreement with our observations. PKC sites include the KCGS motif in repeat 3 (Correas et al., 1992; Steiner, 1993), again with no major effect on microtubule binding in our hands. The partially purified kinase activity described previously (Biernat et al., 1993) phosphorylated all four KXGS motifs, and finally, the kinase activities from brain extract phosphorylated both the Ser/Thr-Pro motifs as well as Ser262 and Ser356 (Gustke et al., 1992), with the reported strong effects on microtubule binding due to Ser262. The strategy employed in these studies was to generate proteolytic fragments from phosphorylated tau which were then separated by HPLC and identified by sequencing. This usually generates a multitude of peptides whose recovery is not always linear, making it difficult to judge the relative amount of phosphorylation at different sites. Because of these uncertainties it was decided to re-investigate the phosphorylation sites by a different approach. The phosphopeptides were analysed not only by HPLC and sequencing, but also by two-dimensional mapping on thin layer cellulose plates which gives a clearer representation of the relative contributions. Full length 4-repeat tau and the repeat domain (K18) were phosphorylated with brain extract, NPK110, PKC, and PKA. This enabled the comparison of the phosphorylation sites in the repeat domain of tau and showed the extent of this phosphorylation in htau40 by each of the kinases. The results are shown in FIG. 9 where the phosphopeptides derived from K18 are labelled according to FIG. 5. Phosphopeptide spots generated by the other kinases were identified by running each sample along with the K18 sample phosphorylated with NPK110 (data not shown).

The patterns shown in FIG. 9A were obtained by phosphorylating full length tau and K18 with brain extract.

With full length tau only spot 1 (Ser262) is clearly seen, spot 2 (Ser356) is barely visible. This is even more prominent in the phosphorylation pattern of K18.

When the phosphorylation of K18 by NPK110 were examined, a peptide pattern similar to that of the brain extract (compare FIGS. 9A and 9B) is formed; the most prominent spots are 1 and 2, containing Ser262 and Ser356, while Ser 305 (spot 3), Ser324 (spot 4), and Ser293 (spot 5) represent minor components. This confirms the role of NPK110 as the major Ser262 kinase. By contrast, re-investigation of the earlier kinase activity (Biernat et al., 1993) has so far yielded inhomogeneous results. Although it phosphorylates the same serines as NPK110 the weighting is different, and the activity of the kinase in brain extract is at least 10-fold lower. This explains why even long incubations of tau with this kinase activity lead to only partial suppression of tau's binding to microtubules, as described earlier.

As seen in FIG. 9C, PKC only phosphorylated Ser305 (spot 3), Ser324 (spot 4) and Ser293 (spot 5) to a significant extent in K18. The smear and the outermost spot to the left (arrow) are not phosphopeptides derived from tau since they also occurred in control experiments where no tau construct had been added (not shown). The remaining two spots could not be identified; the spot on the upper right (starred) did not colocalise with either Ser262 (spot 1) or Ser356 (spot 2). Comparison of this pattern with the one obtained from full length tau revealed that the major phosphorylation sites of PKC are outside the repeat domain. Only Ser305 (spot 3) was faintly visible in this pattern (note that the spot on the upper right does not correspond to the upper right spot from K18 (starred), as confirmed by control experiments (not shown)).

When using purified PKA to phosphorylate full length tau and construct K18 (FIG. 9D) mainly Ser356 (spot 2), Ser305 (spot 3), Ser 324 (spot 4) and Ser293 (spot 5) are found. Ser262 (spot 1) is only a minor phosphorylation site. Phosphorylation of full length tau (FIG. 9D, left panel) yielded similar spots, plus additional sites outside the repeat region of tau. These result are in general agreement with earlier data (Scott et al., 1993; Steiner, 1993). Some of these sites had also been, seen with the "35/41 kDal" kinase activity described previously (Biernat et al., 1993). In subsequent experiments it was determined that the 41 kD component is the catalytic subunit of PKA (using an antibody against PKA obtained from H. Hilz, Hamburg, data not shown); this explains in part the overlap in the data. PKC phosphorylates mainly Ser305, Ser293 and Ser324 (the latter in agreement with Correas et al., 1992), but not Ser262 (FIG. 9C).

EXAMPLE 4

Sites of MAP2 and MAP4 Phosphorylated by the Kinase NPK110

MAP2 and MAP4 are two microtubule-associated proteins which belong to the same MAP-family as tau because they show high homology in the region of the 3 or 4 internal repeats where the proteins bind to microtubules (for review see Chapin & Bulinski, 1992). MAP2 occurs preferentially in brain, mostly in the somatodendritic compartment of neurons. Like tau, MAP2 can be expressed in different forms due to alternative splicing (Kindler et al., 1990): The second repeat may be absent (this is the "classical" MAP2); in addition the region of residues 152–1514 (i.e. 1363 out of 1830 residues) may be absent (generating a protein with 467 residues; this form is commonly called MAP2c). The phosphorylation experiments described here have been performed with recombinant MAP2c expressed in *E. coli* (Table 3).

TABLE 3

| Peaks from second col. | Peptide no. (FIG. 11) | cpm | extinction (214 nm) | peptide sequence | phosphor. residue |
|---|---|---|---|---|---|
| 1 | I | 300,000 | 0.05 | 1705.CGS*LK (SEQ ID NO:8) (in 2nd repeat) | Ser1707 |
| 2 | II | 200,000 | 0.3 | 1674:IGS*TDNIK (SEQ ID NO:9) (in 1st repeat) | Ser1676 |
| 3 | III | 100,000 | 0.8 | 33:DQGGS*GEGLSR (SEQ ID NO:10) | Ser37 |
|  |  |  |  | 1535:SS*LPP (SEQ ID NO:11) | Ser1536 |
| 4 | IV | 100,000 | 0.6 | 1791:LS*NVSS*SGS*IN (SEQ ID NO:12) | Ser1792 Ser1796 Ser1799 |

Note:
Asterisks follow the phosphorylated residue.
The numbering of residues follows that of Albala et al., 1993.

MAP4 is a ubiquitous MAP which is probably involved in mitosis, it also occurs as several splicing isoforms (West et al., 1991). The phosphorylation experiments have been done with a recombinant MAP4 construct comprising the C-terminal 496 residues (including the repeat domain) and expressed in *E. coli* (Table 4).

TABLE 4

| Peaks from second col. | Peptide no. (FIG. 12) | cpm | extinction (214 nm) | peptide sequence | phosphor. residue |
|---|---|---|---|---|---|
| 1 | I | 135,000 | 0.8 | 825:SPATT*LP (SEQ ID NO:13) | Thr829 |
| 2 | II | 150,000 | 0.35 | 939:VGS*TENIK (SEQ ID NO:14) (in 1st repeat) | Ser941 |
| 3 | III | 120,000 | 0.35 | 923:LATTVS*APDLK (SEQ ID NO:15) | Ser928 |
| 4 | IV | 100,000 | 0.8 | 872:NT*T*PT*GAAPP (SEQ ID NO:16) | Thr873 Thr874 Thr876 |
| 5 | V | 55,000 | 0.3 | 898:SS*GALS*VDK (SEQ ID NO:17) | Ser899 Ser903 |
| 6 | VI | 100,000 | 0.8 | 1071:VGS*LD (SEQ ID NO:18) (in 4th repeat) | Ser1073 |

TABLE 4-continued

| Peaks from second col. | Peptide no. (FIG. 12) | cpm | extinction (214 nm) | peptide sequence | phosphor. residue |
|---|---|---|---|---|---|
| 7 | VII | 33,000 | 0.04 | 923:LATTVS*APDLK (SEQ ID NO:19) | Ser928 |

Note:
Asterisks follow the phosphorylated residue.
The numbering of residues follows that of West et al., 1991.

The phosphorylation methods are identical to the ones described in Example 2. MAP2 and MAP4 were phosphorylated with NPK110 using radioactive ATP, the phosphorylated protein was digested with trypsin and analysed by two-dimensional phosphopeptide mapping (FIG. 11 for MAP2c, FIG. 12 for MAP4 construct). The peptides were then purified by two HPLC gradient columns. The purified radioactive peptides were sequenced (for identification of the phosphorylated residues) and identified by two-dimensional phosphopeptide mapping.

Figure 13:
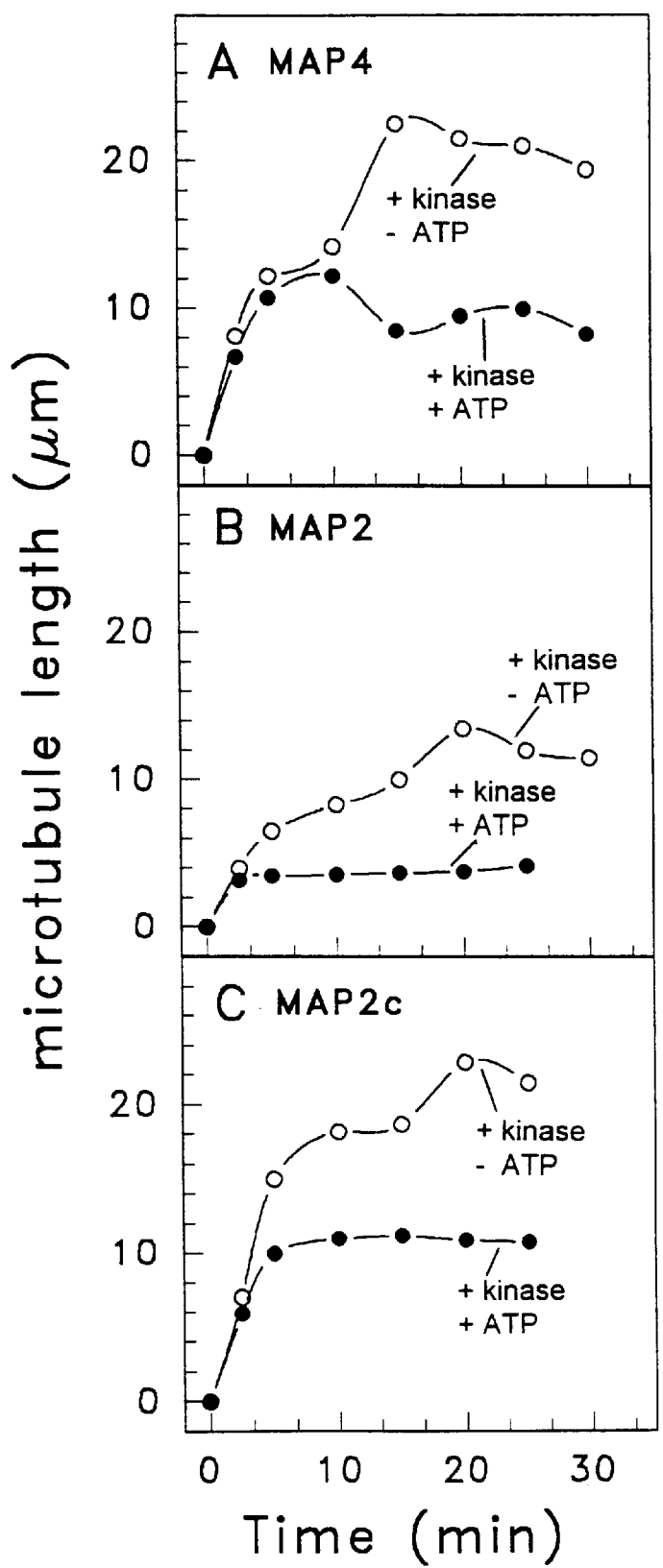

Effects of phosphorylation on interactions with microtubules:

The effects of phosphorylation of MAP2 and MAP4 by NPK110 were the same as for tau, that is, the affinity to microtubules decreased 'several-fold, and the dynamic instability of microtubules became much greater. This can be demonstrated, for example, by the decrease in the mean length of microtubules in the presence of the MAP in question, the kinase NPK110, and ATP (required for phosphorylation). FIG. 13 shows examples for the cases of MAP4, MAP2, and MAP2c. Microtubule assembly starts at time 0. Hollow circles show the increase of mean length in the absence of ATP (no phosphorylation). Filled circles show that in the presence of ATP (and therefore with phosphorylated MAPs) the mean length is only about half of the control.

The biological significance of the novel NPK-110 can be summarised as followed:

NPK-110 is an efficient kinase for the repeat domain of tau, MAP2, MAP2c and MAP4. It phosphorylates all four KXGS motifs in tau, the first and fourth (Ser262 and Ser356) being the most pronounced sites. In this regard the kinase reproduces earlier observations with the kinase activity from the brain extract (Gustke et al., 1992, and see FIG. 9). The most dramatic effects of the kinase are that it virtually eliminates tau,s binding to microtubules (FIG. 6B), it causes the release of tau from microtubules, and it turns stable microtubules into dynamically unstable ones, as seen by video microscopy. These effects are mainly dependent on the phosphorylation of Ser262, as shown by the point mutant Ser262-Ala. These features make NPK110 a candidate enzyme for controlling the state of assembly of microtubules in neurons. They are also consistent with the "Tau Hypothesis of Alzheimer's Disease" which assumes that tau's failure to bind to and'stabilise microtubules leads to their breakdown and cessation of axonal transport. This could occur either by the detachment of tau from microtubules, or by the inhibition of newly synthesised tau to bind to microtubules, in both cases resulting from phosphorylation. According to this scheme, an intervention that would slow down NPK110 or turn off its potential activating cascade would be suitable for a treatment of Alzheimer's disease.

It is furthermore noted that the motif KXGS is conserved not only within the tau repeats, but also within other MAPs such as the neuronal MAP2 and the ubiquitous MAP4 (for review see Chapin & Bulinski, 1992). It is therefore possible that NPK-110 has a more general role, affecting different MAPs and perhaps other proteins. One role which might be envisaged is the involvement of NPK-110 in the generation of cancer.

EXAMPLE 5

Further Characterization of the NPK of the Invention

Description of the cDNA Clones

A screening of a rat brain cDNA library with degenerate oligonucleotides derived from the brain-p110MARK peptide sequences yielded nine clones which were sequenced. They code for at least two different kinases from at least two different genes, with a 70% mutual homology. The peptide sequences fit completely with the larger clone, termed MARK-1 (corresponding to NPK-110), whose 5'-prime end is missing (mol. wt. of the encoded protein approx. 90 kDal). The smaller cDNA MARK-2 encodes a protein of 81 kDal. Peptides suitable for the design of oligonucleotides for screening said cDNA libraries is provided in Table 5. The amino acid sequences of the identified clones are provided in Table 6.

Homologies

A database search for homologous sequences obtained two related but no identical sequences:

MMKEM (X70764), a mouse cDNA encoding a putative protein kinase of unknown function (Inglis et al., 1993), shows 73% homology to MARK-1 and 96%. homology to MARK2.

HUMP78A (M80359), an unpublished human cDNA sequence, shows 73% homology to MARK-1 and 69% homology to MARK-2. All kinases show a low homology (about 25%) to the KIN1 and KIN2 proteins from Saccharomyces cerevisiae (Levin et al., 1987, 1990)

Tissue Distribution

As judged by Northern blotting (FIG. 14), MARK-1 and MARK-2 mRNAs are ubiquitously expressed in fetal and adult tissues. Expression is highest in muscle, brain and fetal (but not adult) kidney.

Activation p110/MARK prepared from brain is at least 100-fold more active than MARK expressed in E. Coli. The activity is dependent on phosporylation of MARK itself on Ser and/or Thr residues, since, after dephosphorylation with phosphatase 2A, all activity is lost.

The phosphorylation of p110/MARK reveals an apparent molecular weight of 110 kD on SDS gels, whereas the predicted molecular weight from CDNA sequencing is 90 kD. This shift in apparent molecular weight is often observed with phosphoproteins.

Targets p110MARK phosphorylates not only tau protein, but also related MAPs such as MAP2 or MAP2c (neuronal MAPs largely confined to the somatodendritic compartment) and MAP4 (a ubiquitous MAP), indicating a widespread function of the enzyme. The major phosphorylation sites are similar in these MAPs, namely the serines in the KXGS motifs in the repeat domain. The effect of phosphorylation is also comparable, namely a strong reduction in the microtubule-binding capacity of the MAPs, and hence a loss of microtubule stability (see FIGS. 15, 16 for examples).

TABLE 5

Peptide sequences obtained from a porcine brain MARK preparation by lysC digestion.

Fraction Sequence:

|  | 1 | 2 | 3 | 4 | 5 | 6 | 7 | 8 | 9 | 10 | 11 | 12 | 13 |
|---|---|---|---|---|---|---|---|---|---|----|----|----|----|
|  | 14 | 15 | 16 | 17 | 18 | 19 | 20 | 21 | | | | | |
| 33–12* | D | R | W | M | N | V | G | H | E | E | E | E | L |
|  | K | P | Y | A | E | P | E | P | | | | | |
|  | (SEQ ID NO:20) | | | | | | | | | | | | |
| 41 | I | A | N | E | L | K | | | | | | | |
|  | (SEQ ID NO:21) | | | | | | | | | | | | |
| 47–16 | A | E | N | L | L | L | D | A | D | M | N | I | K |
|  | (SEQ ID NO:22) | | | | | | | | | | | | |
| 71–09 | X | S | S | R | Q | N | I | P | R | C | R | N | N |
|  | I | I | | | | | | | | | | | |
|  | (SEQ ID NO:23) | | | | | | | | | | | | |

TABLE 5-continued

Peptide sequences obtained from a porcine brain MARK preparation by lysC digestion.

Fraction Sequence:

| 85 | I | L | N | H | P | N | I | V | K | | |
|---|---|---|---|---|---|---|---|---|---|---|---|
|  | (SEQ ID NO:24) | | | | | | | | | | |
| 87–24* | L | D | T | F | C | G | S | P | P | Y | A | A | P |
|  | E | L | F | Q | G | K | | | | | | |
|  | (SEQ ID NO:25) | | | | | | | | | | |
| 120 | L | F | V | L | N | P | I | K | | | |
|  | (SEQ ID NO:26) | | | | | | | | | | |
| 121 | L | F | R | E | V | R | I | X | | | |
|  | (SEQ ID NO:27) | | | | | | | | | | |
| 130–13 | Y | R | I | P | F | Y | M | S | T | D | C | E | N |
|  | (SEQ ID NO:28) | | | | | | | | | | |
| 140–9 | F | R | Q | I | V | S | A | V | Q | Y | C | H | Q |
|  | K | | | | | | | | | | |
|  | (SEQ ID NO:29) | | | | | | | | | | |
| 140–20 | R | I | E | I | M | V | T | M | G | F | L |
|  | (SEQ ID NO:30) | | | | | | | | | | |

TABLE 6

Amino acid sequences corresponding
to the cDNA sequences of MARK-1 and
MARK-2 obtained from a rat
(*Rattus norvegicus*) cDNA library.
MARK-1 (larger, partial cDNA clone)
Total number of residues: 779
MARK-2 (smaller, complete cDNA clone)
Total number of residues: 722.
The character to show that two aligned
residues are identical is '|'

```
MARK-1 - TENHTSVDGYTETHIPP--------TKSSSRQNIPRCRNSITS          -35
           | |              | || |  | ||| ||
MARK-2 - MSS-ARTPLPTLNERDTEQPTLGHLDSKPSSKSNMLRGRNSATS          -43
MARK-1 - ATDEQPHIGNYRLQKTIGKGNFAKVKLARHVLTGREVAVKIIDKTQLNPT    -85
         | |||||||||| |||||||||||||| ||| ||||||||||||||
MARK-2 - A-DEQPHIGNYRLLKTIGKGNFAKVKLARHILTGKEVAVKIIDKTQLNSS    -92
MARK-1 - SLQKLFREVRIMKILNHPNIVKLFEVIETEKTLYLVMEYASGGEVFDYLV    -135
         |||||||||||| |||||||||||||||||||||||||||||||||||
MARK-2 - SLQKLFREVRIMKVLNHPNIVKLFEVIETEKTLYLVMEYASGGEVFDYLV    -142
MARK-1 - AHGRMKEKEARAKFRQIVSAVQYCHQKCIVHRDLKAENLLLDADMNIKIA    -185
         |||||||||||||||||||||||||| | |||||||||||||||||||||
MARK-2 - AHGRMKEKEARAKFRQIVSAVQYCHHKFIVHRDLKAENLLLDADMNIKIA    -192
MARK-1 - DFGFSNEFTVGNKLDTFCGSPPYAAPELFQGKKYDGPEVDVWSLGVILYT    -235
         |||||||| |||||||||||||||||||||||||||||||||||||||||
MARK-2 - DFGFSNEFTFGNKLDTFCGSPPYAAPELFQGKKYDGPEVDVWSLGVILYT    -242
MARK-1 - LVSGSLPFDGQNLKELRERSCLRGKYRVPFYMSTDCENLLKKLLVLNPIK    -285
         ||||||||||||||||||||  |||||| |||||||||||||| | ||| |
MARK-2 - LVSGSLPFDGQNLKELRERV-LRGKYRIPFYMSTDCENLLKKFLILNPSK    -291
MARK-1 - RGSLEQIMKDRWMNVGHEEEELKPYSEPELDLNDAKRIDIMVTMGFARDE    -335
         || ||||||||||||| ||  |||| |  | | |   || ||  ||
MARK-2 - RGTLEQIMKDRWMNVGHEDDELKPYVEPLPDYKDPRRTELMVSMGYTREE    -341
MARK-1 - INDALVSQKYDEVMATYILLGRKPPEFEGGESLSSGNLCQRSRPSSDLNN    -385
         | | || | | |||||| ||| |   | ||           ||| || |
MARK-2 - IQDSLVGQRYNEVMATYLLLGYKSSELEG------DTITLKPRPSADLTN    -385
MARK-1 - STLQSPAHLKVQRTISANQKQRRFSDHAGPSIPPAVSYTKRPQANSVESE    -435
         |   || |||| ||| ||| ||| |||| ||   ||  | || | ||
MARK-2 - SSAPSPSH-KVQRSVSANPKQRRSSDQAVPAIPTSNSYSKKTQSNNAENK    -434
MARK-1 - QKEEWDKDTARRLGSTTVGSKSEVTASPLVGPDRKKSSAGPS-NNVYSGG    -484
```

TABLE 6-continued

Amino acid sequences corresponding
to the cDNA sequences of MARK-1 and
MARK-2 obtained from a rat
(Rattus norvegicus) cDNA library.
MARK-1 (larger, partial cDNA clone)
Total number of residues: 779
MARK-2 (smaller, complete cDNA clone)
Total number of residues: 722.
The character to show that two aligned
residues are identical is '|'

```
           ||    ||        |   ||||| | ||||     || | | |
MARK-2 - RPEE---ETGRK-----ASSTAKVPASPLPGLDRKKTTPTPSTNSVLSTS   -476
MARK-1 - SMTRRNTYVCERSTDRYAALQNGRDSSLTEMSASSMSSTGSTVASAGPSA   -534
           ||      |    |  ||| ||
MARK-2 - TNRSRNSPLLDRASLGQASIQNGKDST----------------------   -503
MARK-1 - RPRHQKSMSTSGHPIKVTLPTIKDGSEAYRPGTAQRVPAASPSAHSISAS   -584
                                          ||||  |||||| || |
MARK-2 - --------------------------------APQRVPVASPSAHNISSS   -521
MARK-1 - T---PDRTRFPRGSSSRSTFHGEQLRERR---SAAYSGPPASPSHDTAALA  -629
           ||||  ||||  ||||||||   |||   |         |||||
MARK-2 - SGAPDRTNFPRGVSSRSTFHAGQLRQVRDQQNLPFGVTPASPS----GHS   -567
MARK-1 - HARRGTSTGIISKITSKFVRRDPSEGEASGRTDTAR----GSSGEPKDKE   -675
           |||  |  |    |   | |    | |       |   |    |
MARK-2 - QGRRGPSGSIFSKFTSKFVRRNLNEPESKDRVETLRPHVVGGGGTDKEKE   -617
MARK-1 - EGKEAKPR-LRFTWSMKTTSSMDPNDMVREIRKVLDANTCDYEQRERFLL   -724
           |   |||||  |||||||||||||| || |  ||||||||||  |    |    ||  |
MARK-2 - EFREAKPRSLRFTWSMTTTSSMEPNEMMREIRKVLDANSCQSELHERYML   -667
MARK-1 - FCVHGDARQDSLVQWEMEVCKLPRLSLNGVRFKRISGTSIAFKNIASKIA   -774
           ||||           |||||||||||||||||||||||||||| ||||||||||
MARK-2 - LCVHGTPGHENFVQWEMEVCKLPRLSLNGVRFKRISGTSMAFKNIASKIA   -717
MARK-1 - NELKL  -779
           |||||
MARK-2 - NELKL  -722
```

REFERENCES

Albala, J. S., Kalcheva, N., Schafit-Zagardo, B. (1993). Characterisation of the transcripts encoding 2 isoforms of human microtubule-associated protein-2 (MAP-2). Gene 136, 377–378.

Anderton, B. H. (1993). Expression and processing of pathological proteins in Alzheimer's disease. Hippocampus 3, 227–237.

Baas, P. W., Pienkowski, T. P., and Kosik, K. S. (1991). Processes induced by tau expression in Sf9-cells have an axon-like microtubule organisation. J. Cell Biol. 115, 1333–1344.

Baumann, K., Mandelkow, E.-M., Biernat, J., Piwnica-Worms, H., Mandelkow, E.(1993). Abnormal Alzheimer-like phosphorylation of tau protein by cyclin-dependent kinases cdk2 and cdk5. FEBS Lett. 336, 417–424.

Berling, B., Wille, H., Röll, B., Mandelkow, E.-M., Garner, C., Mandelkow, E.(1994). Phosphorylation of microtubule-associated proteins MAP2a, b and MAP2c at serine 136 by proline-directed kinases in vivo and in vitro. Eur. J. Cell Biol. 64, 120–130.

Biernat, J., Mandelkow, E.-M., Schröter, C., Lichtenberg-Kraag, B., Steiner, B., Berling, B., Meyer, H. E., Mercken, M., Vandermeeren, A., Goedert, M., Mandelkow, E. (1992). The switch of tau protein to an Alzheimer-like state includes the phosphorylation of two serine-proline motifs upstream of the microtubule binding region. EMBO J. 11, 1593–1597.

Biernat, J., Gustke, N., Drewes, G., Mandelkow, E.-M., Mandelkow, E. (1993). Phosphorylation of serine 262 strongly reduces the binding of tau protein to microtubules: Distinction between PHF-like immunoreactivity and microtubule binding. Neuron 11, 153–163.

Boyle, W. J., van der Geer, P. and Hunter, T. (1991). Phosphopeptide mapping and phosphoamino acid analysis by two-dimensional separation on thin layer cellulose plates. Methods Enzymol. 201, 110–149.

Bramblett, G. T., Goedert, M., Jakes, R., Merrick, S. E., Trojanowski, J. Q., and Lee, V. M. Y. (1993). Abnormal tau phosphorylation at Ser(396) in Alzheimer's disease recapitulates development and contributes to reduced microtubule binding. Neuron 10, 1089–1099.

Brandt, R. and Lee, G. (1993). Functional organisation of microtubule-associated protein tau: Identification of regions which affect microtubule growth, nucleation, and bundle formation in vitro. J. Biol. Chem. 268, 3414–3419.

Brion, J. P., Hanger, D. P., Couck, A. M., and Anderton, B. H. (1991). A68 proteins in Alzheimers-disease are composed of several tau isoforms in a phosphorylated state which affects their electrophoretic mobilities. Biochem. J. 279, 831–836.

Brugg, B., and Matus, A. (1991). Phosphorylation determines the binding of microtubule-associated protein-2 (MAP2) to microtubules in living cells. J. Cell Biol. 114, 735–743.

Butler, M. and Shelanski, M. L. (1986). Microheterogeneity of microtubule-associated tau-proteins is due to differences in phosphorylation. J. Neurochem. 47, 1517–1522.

Butner, K. A., and Kirschner, M. W. (1991). Tau-protein binds to microtubules through a flexible array of distributed weak sites. J. Cell Biol. 115, 717–730.

Casnelli, J. E. (1991). Assay of protein kinases using peptides with basic residues for phosphocellulose binding. Meth. Enzymology 200, 115–120.

Chapin, S. J. and Bulinski, J. C. (1991). Non-neuronal 210 kD Mn microtubule-associated protein (MAP4) contains a domain homologous to the microtubule-binding domains of neuronal MAP2 and tau. J. Cell Sci. 98, 27–36.

Chapin, S. J. and Bulinski, J. C. (1992). Microtubule stabilisation by assembly-promoting microtubule-associated proteins: A repeat performance. Cell Mot. Cytoskel. 23, 236–243.

Chen, J., Kanai, Y., Cowan, N., Hirokawa, N. (1992). Projection domains of MAP2 and tau determine spacings between microtubules in dendrites and axons. Nature 360, 674–677.

Cleveland, D. W., Hwo, S.-Y. and Kirschner, M. W. (1977). Purification of tau, a microtubule-associated protein that induces assembly of microtubules from purified tubulin. J. Mol. Biol. 116, 207–225.

Correas, I., Diaznido, J., and Avila, J. (1992). Microtubule associated protein tau is phosphorylated by protein kinase C on its tubulin binding domain. J. Biol. Chem. 267, 15721–15728.

Drechsel, D. N., Hyman, A. A., Cobb, M. H., and Kirschner, M. W. (1992). Modulation of the dynamic instability of tubulin assembly by the microtubule-associated protein tau. Mol. Biol. Cell 3, 1141–1154.

Drewes, G., Lichtenberg-Kraag, B., Döring, F., Mandelkow, E.-M., Biernat, J., Goris, J., Doree, M. and Mandelkow, E. (1992). Mitogen-activated protein (MAP) kinase transforms tau protein into an Alzheimer like state. EMBO J. 11, 2131–2138.

Drewes, G., Mandelkow, E.-M., Baumann, K., Goris, J., Merlevede, W., Mandelkow, E. (1993). Dephosphorylation of tau protein and Alzheimer paired helical filaments by calcineurin and phosphatase-2A. FEBS Lett. 336, 425–432.

Drubin, D. and Kirschner, M. (1986). Tau protein function in living cells. J. Cell Biol. 103, 2739–2746.

Ennulat, D. J., Liem, R. K. H., Hashim, G. A. and Shelanski, M. L. (1989). Two separate 18-amino acid domains of tau promote the polymerisation of tubulin. J. Biol. Chem. 264 5327–5330.

Geahlen, R. L., Anostario, M., Low, P. S., and Harrison, M. L. (1986). Detection of protein kinase activity in sodium dodedyl sulfate-polyacrylamide gels. Anal. Biochem. 153, 151–158.

Goedert, M., Spillantini, M., Jakes, R., Rutherford, D., and Crowther, R. A. (1989). Multiple isoforms of human microtubule-associated protein-tau: Sequences and localisation in neurofibrillary tangles of Alzheimers-disease. Neuron 3, 519–526.

Goedert, M., Spillantini, G., Cairns, N. J. and Crowther, R. A. (1992). Tau proteins of Alzheimer paired helical filaments: Abnormal phosphorylation of all six brain isoforms. Neuron 8, 159–168.

Goedert, M. (1993). Tau protein and the neurofibrillary pathology of Alzheimer's disease. Trends in Neurosci. 16, 460–465.

Gong, C. X., Singh, T. J., Grundke-Iqbal, I., Iqbal, K. (1994). Alzheimer's disease abnormally phosphorylated tau is dephosphorylated by protein phosphatase-2b (calcineurin). J. Neurochem. 62, 803–806.

Goode, B. L. and Feinstein, S. C. (1994). Identification of a novel microtubule binding and assembly domain in the developmentally regulated inter-repeat region of tau. J. Cell Biol. 124, 769–782.

Greenberg, S. G., Davies, P., Schein, J. D., Binder, L. I. (1992). Hydrofluoric acid-treated tau-PHF proteins display the same biochemical properties as normal tau. J. Biol. Chem. 267, 564–569.

Grundke-Iqbal, I., Iqbal, K., Tung, Y., Quinlan, M., Wisniewski, H., Binder, L.(1986). Abnormal phosphorylation of the microtubule-associated protein tau in Alzheimer cytoskeletal pathology. Proc. Natl. Acad. Sci. U.S.A. 83, 4913–4917.

Gustke, N., Steiner, B., Mandelkow, E.-M., Biernat, J., Meyer, H. E., Goedert, M., Mandelkow, E. (1992). The Alzheimer-like phosphorylation of tau protein reduces microtubule binding and involves Ser-Pro and Thr-Pro motifs. FEBS Letters 307, 199–205.

Gustke, N., Trinczek, B., Biernat, J., Mandelkow, E.-M., Mandelkow, E. (1994). Domains of Tau Protein and Interactions with Microtubules. Biochemistry 33, 9511–9522.

Hagestedt, T., Lichtenberg, B., Wille, H., Mandelkow, E.-M. and Mandelkow, E. (1989). Tau protein becomes long and stiff upon phosphorylation: Correlation between paracrystalline structure and degree of phosphorylation. J. Cell Biol. 109, 1643–1651.

Hanger, D., Hughes, K., Woodgett, J., Brion, J., Anderton, B. (1992). Glycogen-synthase kinase-3 induces Alzheimer's disease-like phosphorylation of tau: Generation of paired helical filament epitopes and neuronal localisation of the kinase. Neurosci. Lett. 147, 58–62.

Hanks, S. K., and Quinn, A. M. (1991). Protein-kinase catalytic domain sequence database: Identification of conserved features of primary structure and classification of family members. Meth. Enzymol. 200, 38–62.

Hasegawa, M., Morishima-Kawashima, M., Takio, K., Suzuki, M., Titani, K., Ihara, Y.(1992). Protein sequence and mass spectrometric analyses of tau in the Alzheimer's disease brain. J. Biol. Chem. 26, 17047–17054.

Himmler, A., Drechsel, D., Kirschner, M. and Martin, D. (1989). Tau consists of a set of proteins with repeated C-terminal microtubule-binding domains and variable N-terminal domains. Molec. Cell. Biol. 9, 1381–1388.

Hirokawa, N. (1994). Microtubule organisation and dynamics dependent on microtubule-associated proteins. Curr. Opinion Cell Biol. 6, 74–81.

Hirs, C. H. W. (1967). Modification of cysteine residues. Methods Enzymol. 11, 325–329.

Inglis, J. D., Lee, M., Hill, R. E. (1993). Emk, a protein-kinase with homologs in yeast maps to mouse chromosome-19. Mamm. Genome 4, 40:1–403.

Ishiguro, K., Omori, A., Sato, K., Tomizawa, K., Imahori, K., and Uchida, T. (1991). A serine threonine proline kinase-activity is included in the tau-protein kinase fraction forming a paired helical filament epitope. Neurosci. Lett. 128, 195–198.

Joly, J. C., and Purich, D. L. (1990). Peptides corresponding to the 2nd repeated sequence in map-2 inhibit binding of microtubule-associated proteins to microtubules. Biochemistry 29, 8916–8920.

Kanemaru, K., Takio, K., Miura, R., Titani, K., and Ihara, Y. (1992). Fetal-type phosphorylation of the tau in paired helical filaments. J. Neurochem. 58, 1667–1675.

Kemp, B. E. and Pearson, R. B. (1990). Protein kinase recognition sequence motifs. TIBS 15, 342–346.

Kindler, S., Schwanke, B., Schulz, B. and Garner, C. C. (1990). Complete cDNA sequence encoding rat high and low molecular weight MAP2. Nucl. Acids Res. 18, 2822.

Kobayashi, S., Ishiguro, K., Omori, A., Takamatsu, M., Arioka, M., Imahori, K., Uchida, T. (1993). A cdc2-related kinase pssalre/cdk5 is homologous with the 30 kDa subunit of tau protein kinase-ii, a proline-directed protein-kinase associated with microtubule. FEBS Letters 335, 171–175.

Kondo, J., Honda, T., Mori, H., Hamada, Y., Miura, R., Ogawara, M. and Ihara, Y. (1988). The carboxyl third of tau is tightly bound to paired helical filaments. Neuron 1, 827–834.

Ksiezak-Reding, H., and Yen, S. H. (1991). Structural stability of paired helical filaments requires microtubule-binding domains of tau: A model for self-association. Neuron 6, 717–728.

Ksiezak-Reding, H., Liu, W. K., and Yen, S. H. (1992). Phosphate analysis and dephosphorylation of modified tau associated with paired helical filaments. Brain Res. 597, 209–219.

Lang, E., Szendrei, G. I., Lee, V. M. Y. and Otvos, L. (1992). Immunological and conformation characterisation of a phosphorylated immunodominant epitope on the paired helical filaments found in Alzheimer's disease. Biochem. Biophys. Res. Comm. 187, 783–790.

Lee, G., Neve, R. L., and Kosik, K. S. (1989). The microtubule binding domain of tau-protein. Neuron 2, 1615–1624.

Lee, V. M. Y., Balin, B. J., Otvos, L., and Trojanowski, J. Q. (1991). A68—a major subunit of paired helical filaments and derivatised forms of normal tau. Science (Wash.) 251, 675–678.

Lee, V. M. Y. and Trojanowski, J. Q. (1992). The disordered neuronal cytoskeleton in Alzheimer's disease. Curr. Opin. Neurobiol. 2, 653–656.

Lee, G. and Rook, S. (1992). Expression of tau protein in non-neuronal cells: microtubule binding and stabilisation. J. Cell Sci. 102, 227–237.

Lee, G. (1993). Non-motor microtubule-associated proteins. Curr. Opin. Cell Biol. 5, 88–94.

Levin, D. E., Bishop, J. M. (1990). A putative protein-kinase gene (kin1+) is important for growth polarity in Schizosaccharomyces pombe. Proc. Natl. Acad. Sci. USA 87, 8272–8276.

Levin, D. E., Hammond, C. I., Ralston, R. O., Bishop, J. M. (1987). Two yeast genes that encode unusual protein kinases. Proc. Natl. Acad. Sci. USA 84, 6035–6039.

Lichtenberg-Kraag, B., Mandelkow, E.-M., Biernat, J., Steiner, B., Schröter, C., Gustke, N., Meyer, H. E., Mandelkow, E. (1992). Phosphorylation dependent interaction of neurofilament antibodies with tau protein: Epitopes, phosphorylation sites, and relationship with Alzheimer tau. Proc. Natl. Acad. Sci. U.S.A. 89, 5384–5388.

Mandelkow, E.-M., Herrmann, M. and Ruhl, U. (1985). Tubulin domains probed by subunit-specific antibodies and limited proteolysis. J. Mol. Biol. 185, 311–327.

Mandelkow, E.-M., Drewes, G., Biernat, J., Gustke, N., Van Lint, J., Vandenheede, J. R. and Mandelkow, E. (1992). Glycogen synthase kinase-3 and the Alzheimer-like state of microtubule-associated protein tau. FEBS Lett. 314, 315–321.

Mandelkow, E.-M. and Mandelkow, E. (1993). Tau as a marker for Alzheimer's disease. TIBS 18, 480–483.

Mercken, M., Vandermeeren, M., Lübke, U., Six, J., Boons, J., Van de Voorde, A., Martin, J.-J. and Gheuens, J. (1992). Monoclonal antibodies with selective specificity for Alzheimer tau are directed against phosphatase-sensitive epitopes. Acta Neuropathol. 84, 265–272.

Meyer, H. E., Hoffmann-Posorske, E. and Heilmeyer, L. M. G. (1991). Determination and location of phosphoserine in proteins and peptides by conversion to S-ethylcysteine. Meth. Enzymol. 201, 169–185.

Paudel, H., Lew, J., Ali, Z., Wang, J. (1993). Brain proline-directed protein kinase phosphorylates tau on sites that are abnormally phosphorylated in tau associated with Alzheimer's paired helical filaments. J. Biol. Chem. 268, 23512–23518.

Schweers, O., Schönbrunn-Hanebeck, E., Marx, A., Mandelkow, E. (1994). Structural studies of tau protein and Alzheimer paired helical filaments show no evidence for β structure. J. Biol. Chem. 269, 24290–24297.

Scott, C., Spreen, R., Herman, J., Chow, F., Davison, M., Young, J., Caputo, C. (1993). Phosphorylation of recombinant tau by cAMP-dependent protein kinase: Identification of phosphorylation sites and effect on microtubule assembly. J. Biol. Chem. 268, 1166–1173.

Steiner, B., Mandelkow, E.-M., Biernat, J., Gustke, N., Meyer, H. E., Schmidt, B., Mieskes, G., Sling, H. D., Drechsel, D., Kirschner, M. W., Goedert, M. and Mandelkow, E. (1990). Phosphorylation of microtubule-associated protein tau: Identification of the site for $Ca^{++}$-calmodulin dependent kinase and relationship with tau phosphorylation in Alzheimer tangles. EMBO J. 9, 3539–3544.

Steiner, B. (1993). Phosphorylation of microtubule-associated protein tau and role in Alzheimer's disease. PhD Thesis, University of Hamburg.

Studier, W. F., Rosenberg, A. H., Dunn, J. J. and Dubendorff, J.W. (1990). Use of T7 RNA polymerase to direct the expression of cloned genes. Meth. Enzym. 185, 60–89.

Tarr, G. E., Black, S. D., Fujita, V. S. and Coon, M. J. (1983). Complete amino acid sequence and predicted membrane topology of phenobarbital-induced cytochrome P-450 isoenzyme 2 from rabbit liver microsomes. Proc. Natl. Acad. Sci. USA 80, 6552–6556.

Trinczek, B., Marx, A., Mandelkow, E.-M., Murphy, D. B. and Mandelkow, E. (1993). Dynamics of microtubules from erythrocyte marginal bands. Molec. Biol. Cell 4, 323–335.

Vulliet, R., Halloran, S., Braun, R., Smith, A., and Lee, G. (1992). Proline-directed phosphorylation of human tau protein. J. Biol. Chem. 267, 22570–22574.

Watanabe, A., Hasegawa, M., Suzuki, M., Takio, K., Morishima-Kawashima, M., Titani, K., Arai, T., Kosik, K. S., and Ihara, Y. (1993). In-vivo phosphorylation sites in fetal and adult rat tau. J. Biol. Chem. 268, 25712–25717.

West, R. R., Tenbarge, K. M., and Olmsted, J. B. (1991). A model for microtubule-associated protein-4 structure: Domains defined by comparisons of human, mouse, and bovine sequences. J. Biol. Chem. 266, 21886–21896.

Wille, H., Drewes, G., Biernat, J., Mandelkow, E.-M., Mandelkow, E. (1992). Alzheimer-like paired helical filaments and antiparallel dimers formed from microtubule-associated protein tau in vitro. J. Cell Biol. 118, 573–584.

Wischik, C., Novak, M., Thogersen, H., Edwards, P., Runswick, M., Jakes, R., Walker, J., Milstein, C, Roth, M. and Klug, A. (1988). Isolation of a fragment of tau derived from the core of the paired helical filament of Alzheimer disease. Proc. Natl. Acad. Sci. U.S.A. 85, 4506–4510.

What is claimed is:

1. A purified and isolated protein kinasepolypeptide, or a functional fragment thereof that phosphorylates an amino acid sequence motif of the type KXGS in tau, MAP4, MAP2, and MAP2c, said polypeptide encoded by a DNA sequence selected from the group consisting of (a) a DNA that encodes the MARK-1 amino acid sequence in SEQ ID NO: 31;

(b) a DNA that encodes the MARK-2 amino acid sequence in SEQ ID NO: 32; or (c) a DNA that encodes a polypeptide with greater than 73% homology to SEQ ID NOs: 31 and a molecular weight of about 90 kDa; or (d) a DNA that encodes a polypeptide with greater than 96% homology to SEQ ID NOs: 32 and a molecular weight of about 81 kDa.

2. The protein kinase polypeptide of claim 1 further characterized in that:

(a) it has an apparent molecular weight of 110 kD as determined by SDS-PAGE;

(b) it phosphorylates serine residues 262, 293, 305,324, and 356 of human tau proteins; and (c) it comprises the following amino acid sequences KLDTFCGSPPYAAPELFQGK (SEQ ID NO: 1) DRWMNVGHEEEELKPYAEP (SEQ ID NO: 2) (K)SSRQNIPRCRNNI (SEQ ID NO: 3).

3. The protein kinase polypeptide of claim 2 further characterized in that:

(d) it is deactivated by phosphatase PP-2A; and
(e) it phosphorylates one or more serine and threonine residues of tau related microtubule associated proteins (MAPs) MAP2, MAP2c, and MAP4 selected from the group consisting of:
MAP2/MAP2c: S37, S1536, S1676, S1707, S1792, S1796, S1799 and
MAP4: T829, T873, T874, T876, S899, S903, S928, S941, S1073
(f) it causes the dissociation of tau, MAP4, MAP2, and MAP2c from microtubules.

4. A diagnostic composition comprising the polypeptide according to claim 1.

5. A method for in vitro phosphorylation of normal MAP2, MAP2c, or MAP4 comprising treating said MAP2, MAP2c or MAP4 with the protein kinase polypeptide, or functional fragment thereof, of claim 1 wherein the MAP2, MAP2c, and MAP4 proteins are phosphorylated at one or more amino acid residues selected from the group consisting of
MAP2/MAP2c: S37, S1536, S1676, S1707, S1792, S1796, S1799 and
MAP4: T829, T873, T874, T876, S899, S903, S928, S941, S1073.

* * * * *

UNITED STATES PATENT AND TRADEMARK OFFICE
CERTIFICATE OF CORRECTION

PATENT NO. : 6,579,691 B1
DATED : June 17, 2003
INVENTOR(S) : Mandelkow et al.

It is certified that error appears in the above-identified patent and that said Letters Patent is hereby corrected as shown below:

<u>Title page,</u>
Item [75], Inventors, please delete "Eva-Marie Mandelkow" and insert -- Eva-Maria Mandelkow --.
Item [73], Assignee, please delete "Forderung" and insert -- Förderung --.
Item [57], ABSTRACT,
Line 7, please delete "NMK" and insert -- NPK --.

<u>Column 49,</u>
Line 2, No. 448, please delete "Arg" and insert -- Leu --.

Signed and Sealed this

Twenty-third Day of March, 2004

JON W. DUDAS
*Acting Director of the United States Patent and Trademark Office*